(12) United States Patent
Kassab et al.

(10) Patent No.: US 9,066,672 B2
(45) Date of Patent: Jun. 30, 2015

(54) SINGLE INJECTION METHODS FOR OBTAINING CONDUCTANCE MEASUREMENTS WITHIN LUMINAL ORGANS USING IMPEDANCE DEVICES

(71) Applicant: 3DT Holdings, LLC, San Diego, CA (US)

(72) Inventors: Ghassan S. Kassab, La Jolla, CA (US); Mark Svendsen, Indianapolis, IN (US); John Browder, Shelbyville, IN (US)

(73) Assignee: 3DT Holdings, LLC, San Diego, CA (US)

( * ) Notice: Subject to any disclaimer, the term of this patent is extended or adjusted under 35 U.S.C. 154(b) by 192 days.

(21) Appl. No.: 13/787,516

(22) Filed: Mar. 6, 2013

(65) Prior Publication Data
US 2013/0184553 A1    Jul. 18, 2013

Related U.S. Application Data

(63) Continuation-in-part of application No. 13/282,906, filed on Oct. 27, 2011, now Pat. No. 8,886,301.

(51) Int. Cl.
*A61B 5/05* (2006.01)
*A61B 5/053* (2006.01)
(Continued)

(52) U.S. Cl.
CPC ............. *A61B 5/0538* (2013.01); *A61B 5/1076* (2013.01); *A61B 5/01* (2013.01); *A61B 5/6853* (2013.01); *A61B 5/7278* (2013.01); *A61B 2017/00026* (2013.01);
(Continued)

(58) Field of Classification Search
USPC ......................................................... 600/547
See application file for complete search history.

(56) References Cited

U.S. PATENT DOCUMENTS 3,896,373 A   7/1975   Zelby
4,380,237 A   4/1983   Newbower
(Continued)

FOREIGN PATENT DOCUMENTS

EP       1 025 805 A1    8/2000
WO       WO 98/35611     8/1998
(Continued)

OTHER PUBLICATIONS

International Searching Authority (ISA), International Search Report and Written Opinion of the ISA, dated Jul. 6, 2005 (PCT/US2004/004828).
(Continued)

*Primary Examiner* — Brian Szmal
(74) *Attorney, Agent, or Firm* — Reichel Stohry LLP; Mark C. Reichel; Natalie J. Dean

(57) ABSTRACT

Single injection methods for obtaining conductance measurements within luminal organs using impedance devices. In at least one method embodiment, the method is performed by introducing at least part of an impedance device into a mammalian luminal organ, the impedance device comprising an elongated body and a detector positioned along the elongated body, obtaining conductance measurements indicative of a fluid native to the mammalian luminal organ and indicative of a fluid injection while the detector is present within and outside of the lumen of the outer sheath, and calculating a size parameter of the mammalian luminal organ based in part upon some of the obtained conductance measurements.

21 Claims, 14 Drawing Sheets

(51) Int. Cl.
  *A61B 5/107* (2006.01)
  *A61B 5/00* (2006.01)
  A61B 5/01 (2006.01)
  A61B 17/00 (2006.01)
  A61B 17/22 (2006.01)
  A61B 18/22 (2006.01)

(52) U.S. Cl.
  CPC ............... *A61B 2017/22051* (2013.01); *A61B 2018/2238* (2013.01); *A61B 2017/00084* (2013.01)

(56) References Cited

U.S. PATENT DOCUMENTS

| | | |
|---|---|---|
| 4,587,975 A | 5/1986 | Salo et al. |
| 4,840,182 A | 6/1989 | Carlson |
| 4,873,987 A | 10/1989 | Djordjevich et al. |
| 4,957,110 A | 9/1990 | Vogel et al. |
| 5,058,583 A | 10/1991 | Geddes et al. |
| 5,125,410 A | 6/1992 | Misono et al. |
| 5,233,994 A | 8/1993 | Shmulewitz |
| 5,366,443 A | 11/1994 | Eggers et al. |
| 5,453,576 A | 9/1995 | Krivitski |
| 5,665,103 A | 9/1997 | Lafontaine et al. |
| 5,827,192 A | 10/1998 | Gopakumaran et al. |
| 5,842,998 A | 12/1998 | Gopakumaran et al. |
| 5,971,933 A | 10/1999 | Schluter et al. |
| 6,112,115 A | 8/2000 | Feldman et al. |
| 6,165,977 A | 12/2000 | Mochly-Rosen |
| 6,187,744 B1 | 2/2001 | Rooney |
| 6,191,136 B1 | 2/2001 | Marban |
| 6,270,493 B1 | 8/2001 | Lalonde et al. |
| 6,325,762 B1 | 12/2001 | Tjin |
| 6,354,999 B1 | 3/2002 | Dgany et al. |
| 6,360,123 B1 | 3/2002 | Kimchi et al. |
| 6,398,738 B1 | 6/2002 | Millar |
| 6,471,656 B1 | 10/2002 | Shalman et al. |
| 6,494,832 B1 | 12/2002 | Feldman et al. |
| 6,511,413 B2 | 1/2003 | Landesberg |
| 6,545,678 B1 | 4/2003 | Ohazama |
| 6,569,862 B1 | 5/2003 | Marban |
| 6,663,661 B2 | 12/2003 | Boneau |
| 6,666,828 B2 | 12/2003 | Greco et al. |
| 6,926,674 B2 | 8/2005 | Tenerz et al. |
| 6,939,313 B2 | 9/2005 | Saadat |
| 7,069,072 B2 | 6/2006 | Jansen et al. |
| 7,141,019 B2 | 11/2006 | Pearlman |
| 7,169,107 B2 | 1/2007 | Jersey-Willhun et al. |
| 7,189,208 B1 | 3/2007 | Beatty et al. |
| 7,236,820 B2 | 6/2007 | Mabary et al. |
| 7,311,702 B2 | 12/2007 | Tallarida et al. |
| 7,326,241 B2 | 2/2008 | Jang |
| 2002/0049488 A1 | 4/2002 | Boneau |
| 2004/0024329 A1 | 2/2004 | Jansen et al. |
| 2004/0254495 A1 | 12/2004 | Mabary et al. |
| 2007/0161914 A1 | 7/2007 | Zdeblick et al. |
| 2008/0176271 A1 | 7/2008 | Silver et al. |
| 2008/0194996 A1 | 8/2008 | Kassab |
| 2008/0269581 A1 | 10/2008 | Wood et al. |
| 2009/0216133 A1 | 8/2009 | Kassab |
| 2010/0041984 A1 | 2/2010 | Shapeland et al. |

FOREIGN PATENT DOCUMENTS

| | | |
|---|---|---|
| WO | WO 02/19905 | 3/2002 |
| WO | WO 02/085442 | 10/2002 |
| WO | WO 03/092495 A1 | 11/2003 |

OTHER PUBLICATIONS

International Searching Authority (ISA), International Search Report and Written Opinion of the ISA, dated Aug. 8, 2007 (PCT/US2006/005985).

PCT International Preliminary Report on Patentability, dated Oct. 18, 2011 (PCT/US2010/031553).

PCT International Preliminary Report on Patentability, dated Nov. 3, 2011 (PCT/US2010/032178).

International Searching Authority, International Search Report, dated Apr. 4, 2011 (PCT/US2011/023911).

International Searching Authority, Written opinion of the International Searching Authority, dated Apr. 4, 2011 (PCT/US2011/023911).

International Searching Authority, International Search Report, dated Jul. 7, 2011 (PCT/US2011/024961).

International Searching Authority, Written opinion of the International Searching Authority, dated Jul. 7, 2011 (PCT/US2011/024961).

International Searching Authority, International Search Report, dated Apr. 19, 2011 (PCT/US2011/026337).

International Searching Authority, Written opinion of the International Searching Authority, dated Apr. 19, 2011 (PCT/US2011/026337).

Supplementary European Search Report for EP application Serial No. 04 71 2383 to Electro-Cat, LLC, dated Aug. 3, 2007.

Hoekstein and Inbar, "Cardiac Stroke Volume Estimation . . . " Technion Department of Electrical Engineering Publication EE PUB No. 991, Feb. 1994.

L. Kornet, et al. "Conductance Method for the Measurement of . . . " Annals of Biomedical Engineering, vol. 27. pp. 141-150, 1999.

Douglas A. Hettrick, et al. "Finite Element Model Determination of . . . " Annals of Biomedical Engineering. vol. 27, pp. 151-159, 1999.

Douglas A. Hettrick, et al. "In Vivo Measurement of Real-Time Aortic Segmental Volume . . . " Annals of Biomedical Engineering. vol. 26, pp. 431-440, 1998.

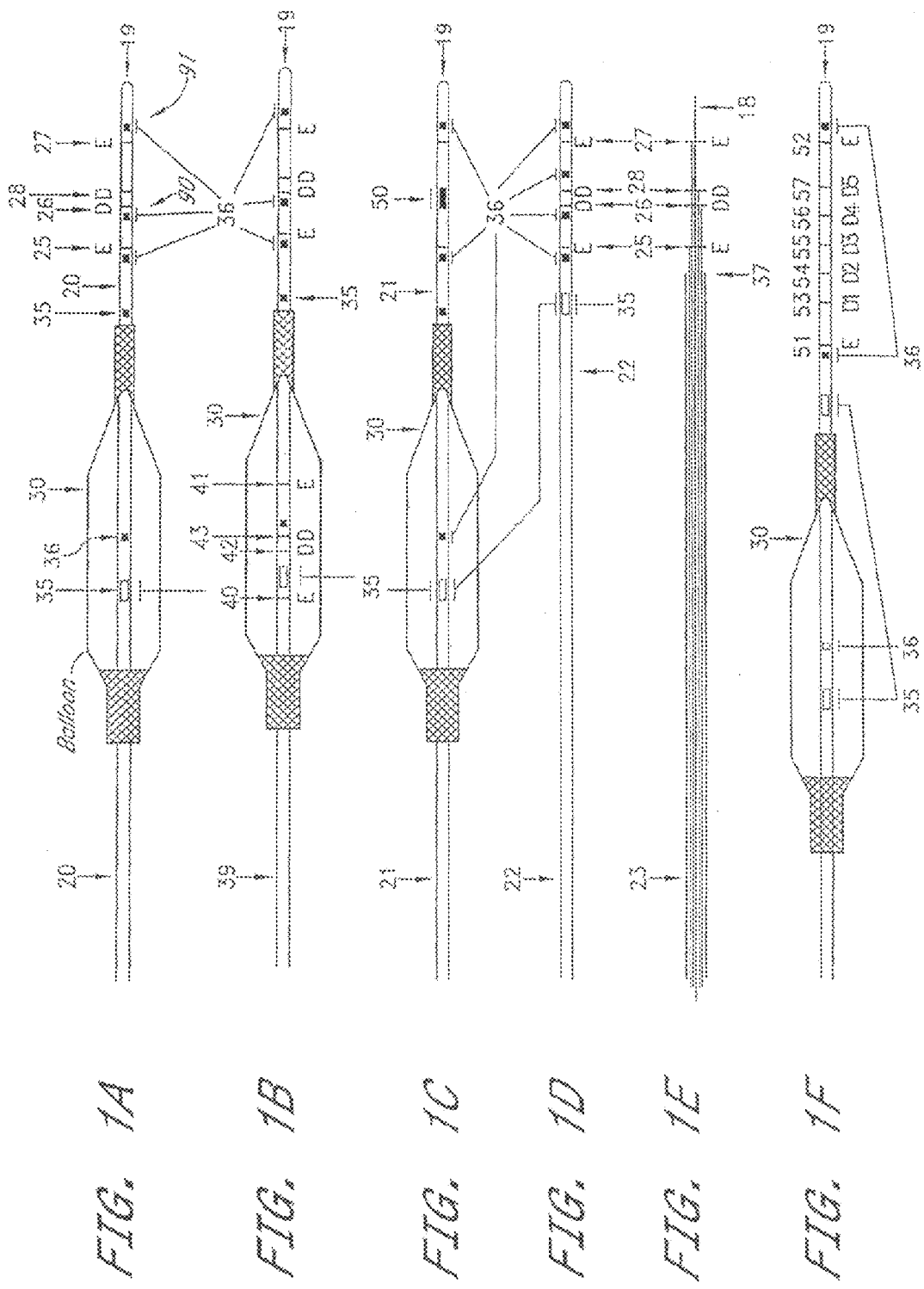

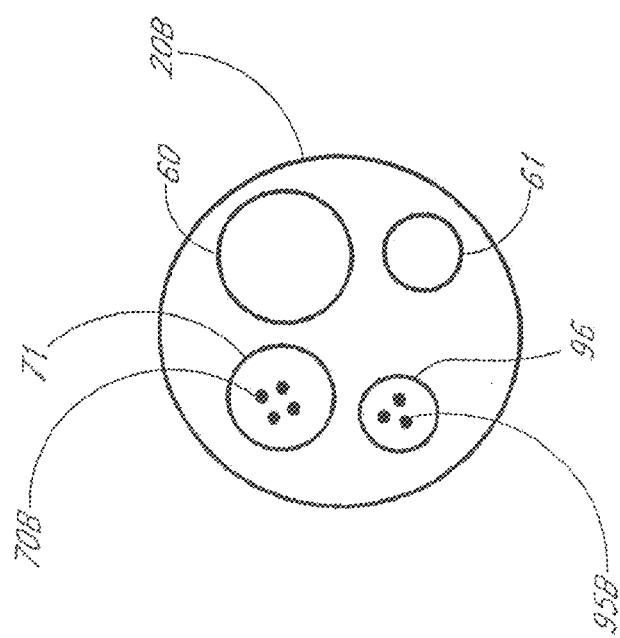
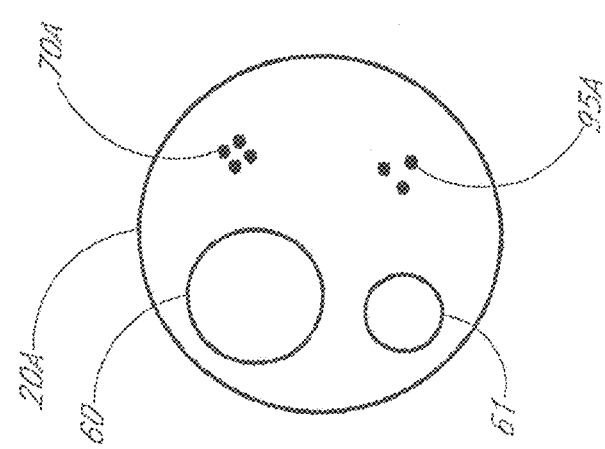

envelope data peak-peak of voltage at the detection electrodes

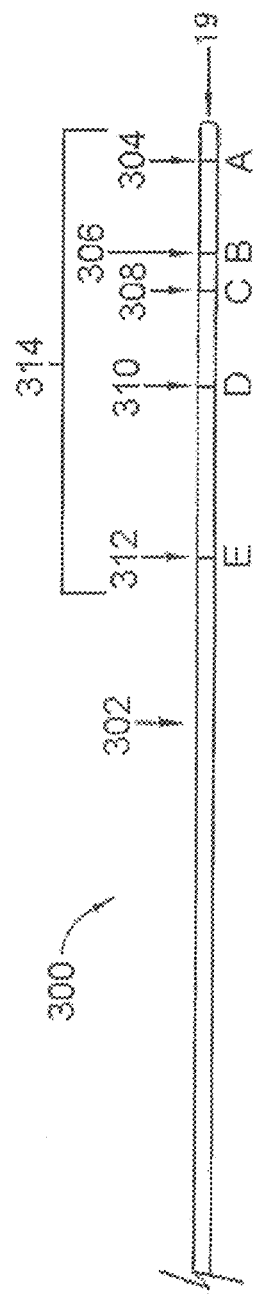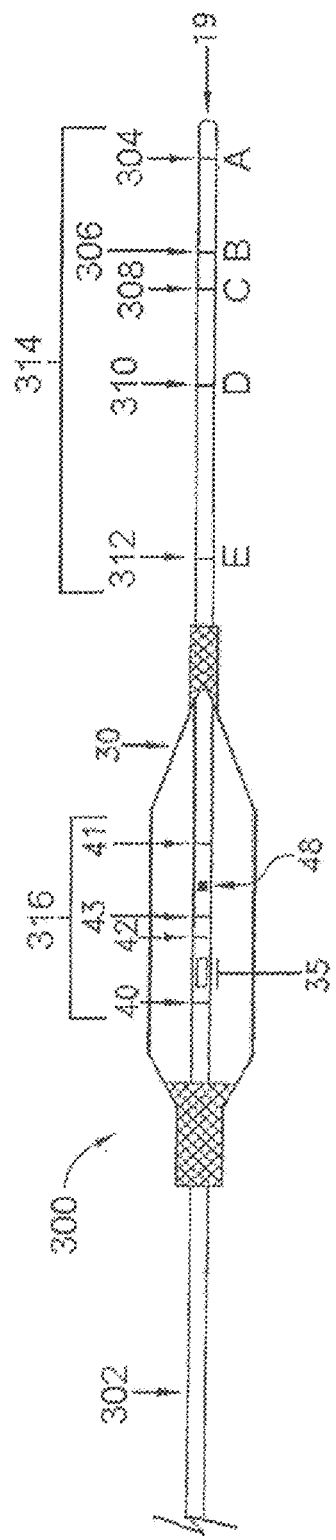

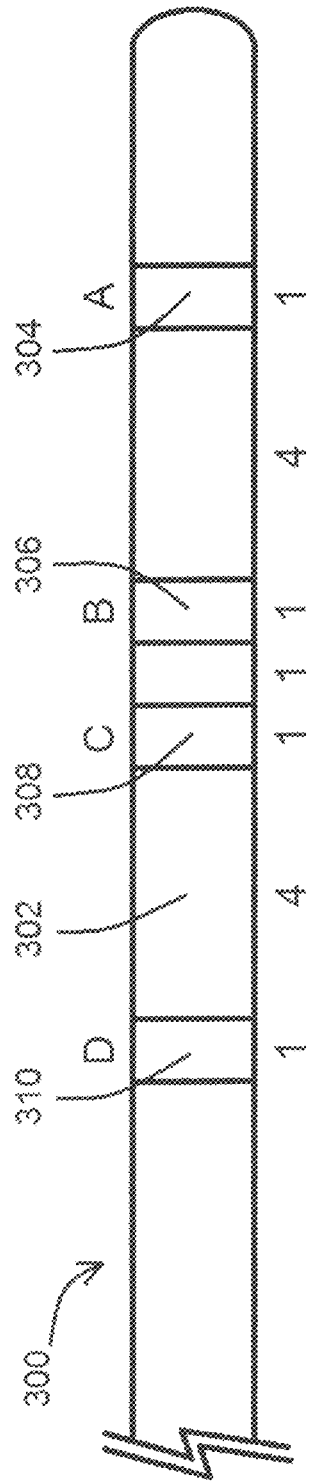
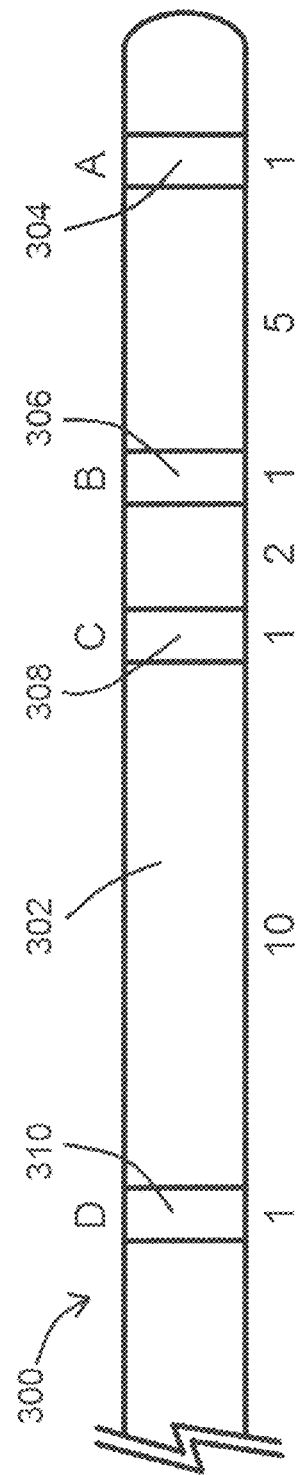
FIG. 9A
FIG. 9B

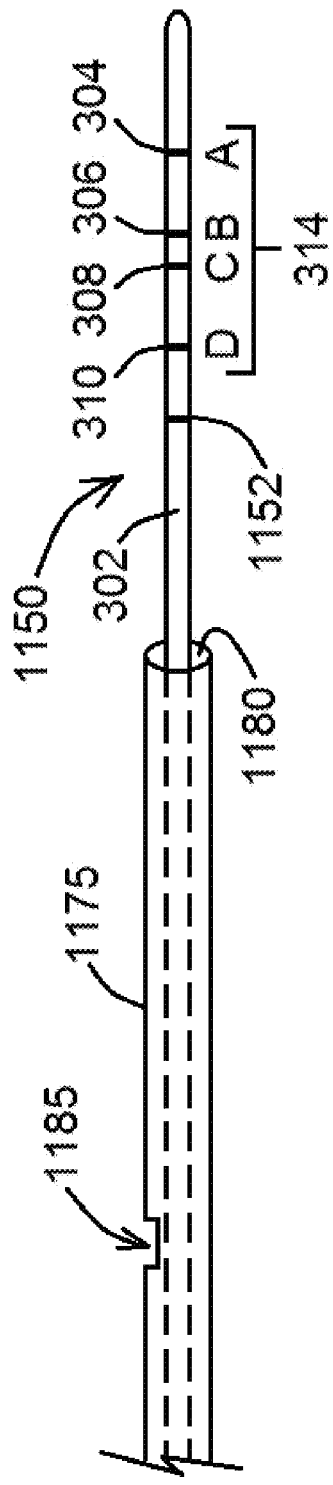
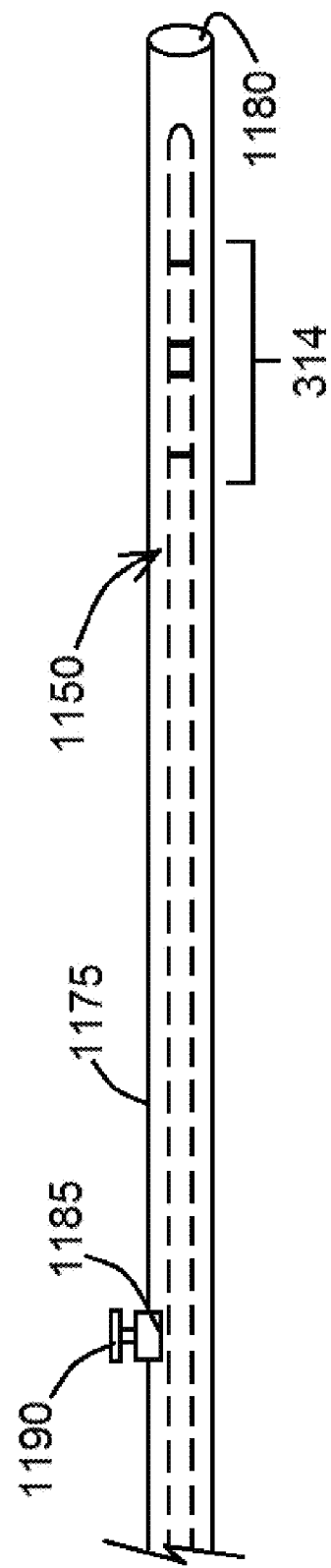
FIG. 11A
FIG. 11B

SINGLE INJECTION METHODS FOR OBTAINING CONDUCTANCE MEASUREMENTS WITHIN LUMINAL ORGANS USING IMPEDANCE DEVICES

PRIORITY

This U.S. patent application is related to, claims the priority benefit of, and is a continuation-in-part application of, U.S. patent application Ser. No. 13/282,906, filed Oct. 27, 2011, which is related to, claims the priority benefit of, and is a continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a divisional application of, U.S. patent application Ser. No. 10/782,149, filed Feb. 19, 2004 and issued as U.S. Pat. No. 7,454,244 on Nov. 18, 2008, which is related to, and claims the priority benefit of, U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003. The contents of each of these applications are hereby incorporated by reference in their entirety into this disclosure.

BACKGROUND

The present disclosure relates generally to medical diagnostics and treatment equipment, including, but not limited to, devices for measuring luminal cross-sectional areas of blood vessels, heart valves and other hollow visceral organs, and methods of using the same.

Coronary Heart Disease

Coronary heart disease is caused by atherosclerotic narrowing of the coronary arteries. It is likely to produce angina pectoris, heart attack or both. Coronary heart disease caused 466,101 deaths in USA in 1997 and is the single leading cause of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angio-graphically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

BRIEF SUMMARY

The present disclosure provides for various devices and systems for measuring cross-sectional areas and pressure gradients in luminal organs. The present disclosure also comprises a method and apparatus for measuring cross-sectional areas and pressure gradients in luminal organs, such as, for example, blood vessels, heart valves, and other visceral hollow organs.

In at least one embodiment, an exemplary system of the present disclosure comprises an impedance catheter capable of being introduced into a treatment site, a solution delivery source for injecting a solution through the catheter into the treatment site, a constant current source enabling the supply of constant electrical current to the treatment site, and a data acquisition system enabling the measurement of parallel conductance at the treatment site, whereby enabling calculation of cross-sectional area at the treatment site.

In at least one embodiment of a method for obtaining one or more conductance measurements using an impedance device, the method comprising the steps of introducing at least part of an impedance device into a mammalian luminal organ, the impedance device comprising an elongated body and a detector positioned along the elongated body, obtaining a first conductance measurement using the detector while the detector is surrounded by an outer sheath surrounding at least part of the impedance device, the first conductance measurement indicative of a fluid native to the mammalian luminal organ present within a lumen of the outer sheath, obtaining a second conductance measurement using the detector while the detector is surrounded by the outer sheath, the second conductance measurement indicative of a first injection of a first solution of a first compound through the lumen of the outer sheath, moving the impedance device and/or the outer sheath relative to one another so that the outer sheath no longer surrounds the detector, obtaining a third conductance measurement using the detector, the third conductance measurement indicative of the fluid native to the mammalian luminal organ, obtaining a fourth conductance measurement using the detector, the fourth conductance measurement indicative of a second injection of the first solution through the lumen of the outer sheath, and calculating a size parameter of the mammalian luminal organ based in part upon the third conductance measurement, the fourth conductance measurement, and a conductivity of the fluid native to the mammalian luminal organ determined in part from the first conductance measurement. In another embodiment, the step of introducing the at least part of the impedance device is performed using access through a patient's femoral artery and advancement to a location of interest within the mammalian luminal organ. In yet another embodiment, the step of obtaining the first conductance measurement is performed while an aperture defined within the outer sheath is opened to allow the fluid native to the mammalian luminal organ to flow within the lumen of the outer sheath. In an additional embodiment, the step of obtaining the first conductance measurement is performed while the fluid native to the mammalian luminal organ is pulled into the lumen of the outer sheath using suction.

In at least one embodiment of a method for obtaining one or more conductance measurements using an impedance device, the step of obtaining the second conductance measurement is performed when a desired temperature local to the detector is achieved, the desired temperature indicative of the first injection of the first solution. In an additional embodiment, the desired temperature is determined using a temperature sensor coupled to the impedance device at or near the detector. In yet an additional embodiment, the step of obtaining the second conductance measurement is performed when a threshold conductance is achieved, the threshold conductance indicative of a conductance sufficiently different from the first conductance measurement. In another embodiment, the step of calculating a size parameter comprises calculating a conductivity of fluid native to the mammalian luminal organ based in part upon the first conductance measurement and the second conductance measurement.

In at least one embodiment of a method for obtaining one or more conductance measurements using an impedance device, the method further comprises the step of calibrating the impedance device prior to the step of introducing the at least part of the impedance device into the mammalian organ, the step of calibrating performed by operating the device within a plurality of phantoms of known sizes in the presence of the first solution to determine a conductivity of the first solution. In another embodiment, the step of calculating a size parameter is performed using the conductivity of the fluid native to the mammalian luminal organ which is further determined from second conductance measurement and the conductivity of the first solution. In various embodiments, the step of calculating a size parameter is performed using the conductivity of the fluid native to the mammalian luminal organ which is further determined using a known inner cross-sectional area of the outer sheath and a known distance between detection electrodes of the detector. In yet another embodiment, the step of obtaining the fourth conductance measurement is performed when a desired temperature local to the detector is achieved, the desired temperature indicative of the second injection of the first solution. In an additional embodiment, the step of obtaining the fourth conductance measurement is performed by obtaining a plurality of fourth conductance measurements over time.

In at least one embodiment of a method for obtaining one or more conductance measurements using an impedance device, the step of calculating a size parameter is further based in part upon a known distance between detection electrodes of the detector. In an additional embodiment, the introducing step is performed by introducing an impedance device selected from the group consisting of an impedance catheter and an impedance wire into the mammalian luminal organ, wherein the impedance device is at least partially surrounded by an outer sheath selected from the group consisting of catheter and a non-catheter sheath. In yet an additional embodiment, the step of introducing is performed by introducing the at least part of the impedance device into the mammalian luminal organ at or near a stenosis, whereby the impedance device can be used to perform one or more of the steps of obtaining a third conductance measurement and/or obtaining a fourth conductance measurement at or near the stenosis. In another embodiment, the step of introducing is performed by introducing the at least part of the impedance device into the mammalian luminal organ at or near a stenosis, and the method further comprises the steps of moving the at least part of the impedance device to a second location within the mammalian luminal organ, obtaining a fifth conductance measurement using the detector, the fifth conductance measurement indicative of the fluid native to the mammalian luminal organ at the second location, obtaining a sixth conductance measurement using the detector, the sixth conductance measurement indicative of a third injection of the first solution through the lumen of the outer sheath, and calculating a second size parameter of the mammalian luminal organ at the second location based in part upon the first conductance measurement, the second conductance measurement, the fifth conductance measurement, and the sixth conductance measurement, wherein the third conductance measurement and the fourth conductance measurement are indicative of one of a stenotic lesion or a non-stenotic region, and wherein the fifth conductance measurement and the sixth conductance measurement are indicative of the other of the stenotic lesion or the non-stenotic region. In yet another embodiment, the step of calculating a size parameter is performed to calculate a size parameter selected from the group consisting of a cross-sectional area, a diameter, and a radius.

In at least one embodiment of a method for obtaining one or more conductance measurements using an impedance device, the method comprises the steps of introducing at least part of an impedance device into a mammalian luminal organ, the impedance device comprising an elongated body and a detector positioned along the elongated body, obtaining a first conductance measurement using the detector while the detector is surrounded by an outer sheath surrounding at least part of the impedance device, the first conductance measurement indicative of blood from the mammalian luminal organ present within a lumen of the outer sheath, obtaining an optional second conductance measurement using the detector while the detector is surrounded by the outer sheath, the second conductance measurement indicative of a first injection of saline through the lumen of the outer sheath, moving the impedance device and/or the outer sheath relative to one another so that the outer sheath no longer surrounds the detector, obtaining a third conductance measurement using the detector, the third conductance measurement indicative of the blood, obtaining a fourth conductance measurement using the detector, the fourth conductance measurement indicative of a second injection of the saline through the lumen of the outer sheath, and calculating a size parameter of the mammalian luminal organ based in part upon the third conductance measurement, the fourth conductance measurement, and a conductivity of the fluid native to the mammalian luminal organ determined in part from the first conductance measurement. In an additional embodiment, the introducing step is performed by introducing an impedance device selected from the group consisting of an impedance catheter and an impedance wire into the mammalian luminal organ, wherein the impedance device is at least partially surrounded by an outer sheath selected from the group consisting of catheter and a non-catheter sheath.

In at least one embodiment of a method for obtaining one or more conductance measurements using an impedance device, the method comprises the steps of introducing at least part of an impedance device into a mammalian luminal organ, the impedance device comprising an elongated body and a detector positioned along the elongated body, obtaining a first conductance measurement using the detector while the detector is surrounded by an outer sheath surrounding at least part of the impedance device, the first conductance measurement indicative of a fluid native to the mammalian luminal organ present within a lumen of the outer sheath, obtaining a second conductance measurement using the detector while the detector is surrounded by the outer sheath, the second conductance measurement indicative of a first injection of a first solution of a first compound through the lumen of the outer sheath, moving the impedance device and/or the outer sheath relative to one another so that the outer sheath no longer surrounds the detector, obtaining a third conductance measurement using the detector, the third conductance measurement indicative of the fluid native to the mammalian luminal organ, obtaining a fourth conductance measurement using the detector, the fourth conductance measurement indicative of a second injection of the first solution through the lumen of the outer sheath, moving the at least part of the impedance device to a second location within the mammalian luminal organ, obtaining a fifth conductance measurement using the detector, the fifth conductance measurement indicative of the fluid native to the mammalian luminal organ at the second location, obtaining a sixth conductance measurement using the detector, the sixth conductance measurement indicative of a third injection of the first solution through the lumen of the outer sheath, calculating a first size parameter of the mammalian luminal organ based in part upon the third conductance measurement, the fourth conductance measurement, and a conductivity of the fluid native to the mammalian luminal organ determined in part from the first conductance measurement, and calculating a second size parameter of the mammalian luminal organ at the second location based in part upon the fifth conductance measurement and the sixth conductance measurement.

BRIEF DESCRIPTION OF THE DRAWINGS

FIG. 1A shows a balloon catheter having impedance measuring electrodes supported in front of the stenting balloon, according to an embodiment of the present disclosure;

FIG. 1B shows a balloon catheter having impedance measuring electrodes within and in front of the balloon, according to an embodiment of the present disclosure;

FIG. 1C shows a catheter having an ultrasound transducer within and in front of balloon, according to an embodiment of the present disclosure;

FIG. 1D shows a catheter without a stenting balloon, according to an embodiment of the present disclosure;

FIG. 1E shows a guide catheter with wire and impedance electrodes, according to an embodiment of the present disclosure;

FIG. 1F shows a catheter with multiple detection electrodes, according to an embodiment of the present disclosure;

FIG. 2A shows a catheter in cross-section proximal to the location of the sensors showing the leads embedded in the material of the probe, according to an embodiment of the present disclosure;

FIG. 2B shows a catheter in cross-section proximal to the location of the sensors showing the leads run in separate lumens, according to an embodiment of the present disclosure;

FIG. 8A shows an exemplary device operable to obtain one or more sizing measurements and one or more fluid velocity measurements, according to an embodiment of the present disclosure;

FIG. 8B shows an exemplary device with a balloon coupled thereto, the device operable to obtain one or more sizing measurements and one or more fluid velocity measurements, according to an embodiment of the present disclosure;

FIGS. 9A-10B show exemplary devices having various numbers of electrodes and various spacings therebetween, according to exemplary embodiments of the present disclosure;

FIGS. 11A and 11B show exemplary devices of the present disclosure with the detector outside of an outer sheath and inside of an outer sheath, respectively, according to exemplary embodiments of the present disclosure;

DETAILED DESCRIPTION

Figure 3:
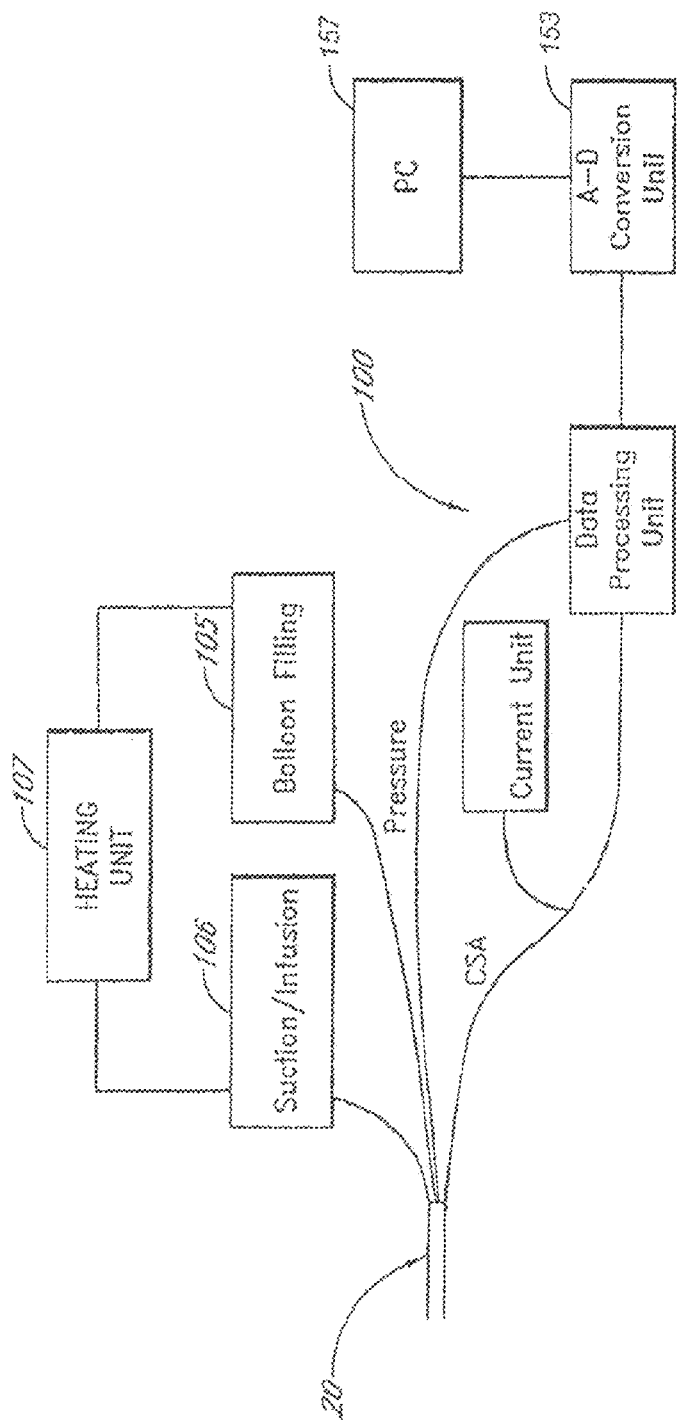
FIG. 3 is a schematic of one embodiment of the system showing a catheter carrying impedance measuring electrodes connected to the data acquisition equipment and excitation unit for the cross-sectional area measurement, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This present disclosure makes accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the present disclosure overcome the problems associated with determination of the size (cross-sectional area) of luminal organs, such as, for example, in the coronary arteries, carotid, femoral, renal and iliac arteries, aorta, gastrointestinal tract, urethra and ureter. Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Device and System Embodiments

We designed and build the impedance or conductance catheters illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In the preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, Catheter 20 advantageously includes pressure port 90 and pressure port 91 proximal to or at the site of the cross-sectional measurement for evaluation of pressure gradients. As described below with reference to FIGS. 2A, 2B and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry. One or more fiber-optic sensors may be used as an exemplary electrode or sensor of the present disclosure.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27 and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D shows an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter contains an extra channel for insertion of a guide wire to stiffen the flexible catheter during the insertion or data recording. In yet another embodiment (not illustrated), the catheter includes a sensor for measurement of the flow of fluid in the body organ.

System for Determining Cross-Sectional Area and Pressure Gradient

The Operation of the Impedance Catheter 20 is as Follows:

With reference to the embodiment shown in FIG. 1A for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue), and $C_b$ is the specific electrical conductivity of the bodily fluid which for blood generally depends on the temperature, hematocrit and orientation and deformation of blood cells and L is the distance between the detection electrodes. Equation [1] can be rearranged to solve for cross sectional area CSA(t), with a correction factor, $\alpha$, if the electric field is non-homogeneous, as $$CSA(z, t) = \frac{L}{\alpha C_b}[G(z, t) - G_p(z, t)] \quad [1b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that $\alpha$ is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two Equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation [1]

allows the calculation of the specific electrical conductivity of blood in the presence of blood flow as $$C_b = \frac{L}{CSA(z, t)}[G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity U. Equation [1b] can be expressed as $$CSA(U \cdot t, t) = \frac{L}{C_b}[G(U \cdot t, t) - G_p(U \cdot (t, t)] \quad [7]$$

where the axial position, z, is the product of catheter velocity, U, and time, t; i.e., z=U·t.

For the two injections, denoted by subscript "1" and subscript "2", respectively, we can consider different time points T1, T2, etc. such that Equation [7] can be written as $$CSA_1[U \cdot T_1, t) = \frac{L}{C_1}[G_1(U \cdot T_1, t) - G_{p1}(U \cdot t_1, t)] \quad [8a]$$

$$CSA_1(U \cdot T_1, t) = \frac{L}{C_2}[G_2(U \cdot T_1, t) - G_{p1}(U \cdot t_1, t)] \quad [8b]$$

and $$CSA_2(U \cdot T_2, t) = \frac{L}{C_1}[G_1(U \cdot T_2, t) - G_{p2}(U \cdot T_2, t)] \quad [8c]$$

$$CSA_2(U \cdot T_2, t) = \frac{L}{C_2}[G_2(U \cdot T_2, t) - G_{p2}(U \cdot T_2, t)] \quad [8d]$$

and so on. Each set of Equations [8a], [8b] and [9a], [9b], etc. can be solved for $CSA_1$, $G_{p1}$ and $CSA_2$, $G_{p2}$, respectively. Hence, we can measure the CSA at various time intervals and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a 3-Dimensional vessel on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the Impedance Catheter 39:

With reference to the embodiment shown in FIG. 1B, the voltage difference between the detection electrodes 42 and 43 depends on the magnitude of the current (I) multiplied by the distance (D) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following Equations:

$$\Delta V = \frac{I \cdot L}{C \cdot CSA} \quad [10a]$$

or $$CSA = \frac{G \cdot L}{C} \quad [10b]$$

where G is conductance expressed as the ratio of current to voltage (I/ΔV). Equation [10] is identical to Equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

With reference to FIG. 3, in one embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The CSA and parallel conductance and other relevant measures such as distensibility, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying the 2D or 3D-geometry of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the current amplifier, which may be a constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_w$ is the wall area of the organ and $C_w$ is the electrical conductivity through the wall. This Equation can be solved for the wall $CSA_w$ as $$h = \frac{CSA_w}{\pi D} \quad [12]$$

For a cylindrical organ, the wall thickness, h, can be expressed as $$CSA_w = \frac{G_p \cdot L}{C_w} \quad [11b]$$

where D is the diameter of the vessel which can be determined from the circular CSA ($D=[4CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., $P \cdot r$, where P and r are the intraluminal pressure and radius of a cylindrical organ), stress (e.g., $P \cdot r/h$ where h is the wall thickness of the cylindrical organ), strain (e.g., $(C-C_d)/C_d$ where C is the inner circumference and $C_d$ is the circumference in diastole) and wall shear stress (e.g., $4\mu Q/r^3$ where $\mu$, Q and r are the fluid viscosity, flow rate and radius of the cylindrical organ for a fully developed flow). These quantities can be used in assessing the mechanical characteristics of the system in health and disease.

Method

In one approach, luminal cross-sectional area is measured by introducing a catheter from an exteriorly accessible opening (e.g., mouth, nose or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a sampling frequency of 75 KHz, with two channels—the current injected and the detected voltage, respectively. The current injected has a frequency of 5 KH, so the voltage detected, modulated in amplitude by the impedance changing through the bolus injection will have a spectrum in the vicinity of 5 KHz.

Figure 4A:
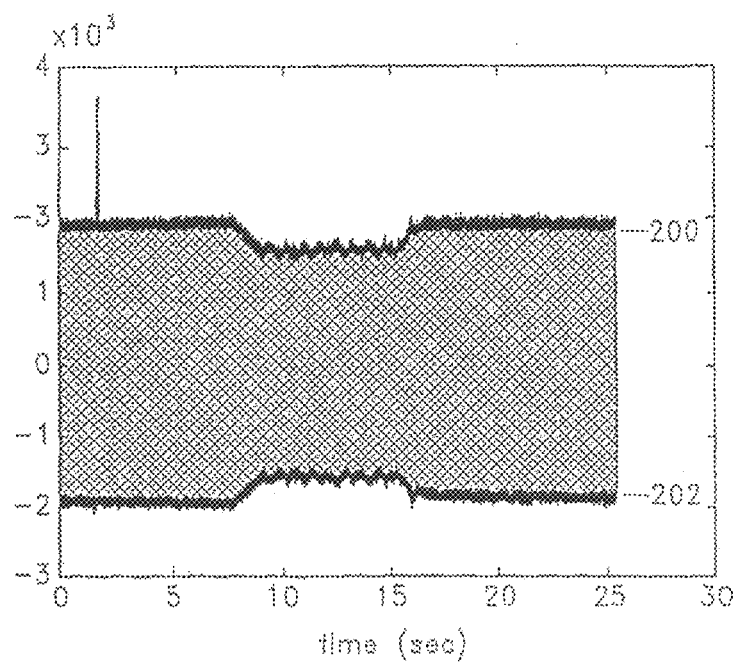
FIG. 4A shows the detected filtered voltage drop as measured in the blood stream before and after injection of 1.5% NaCl solution, according to an embodiment of the present disclosure.
Figure 4B:
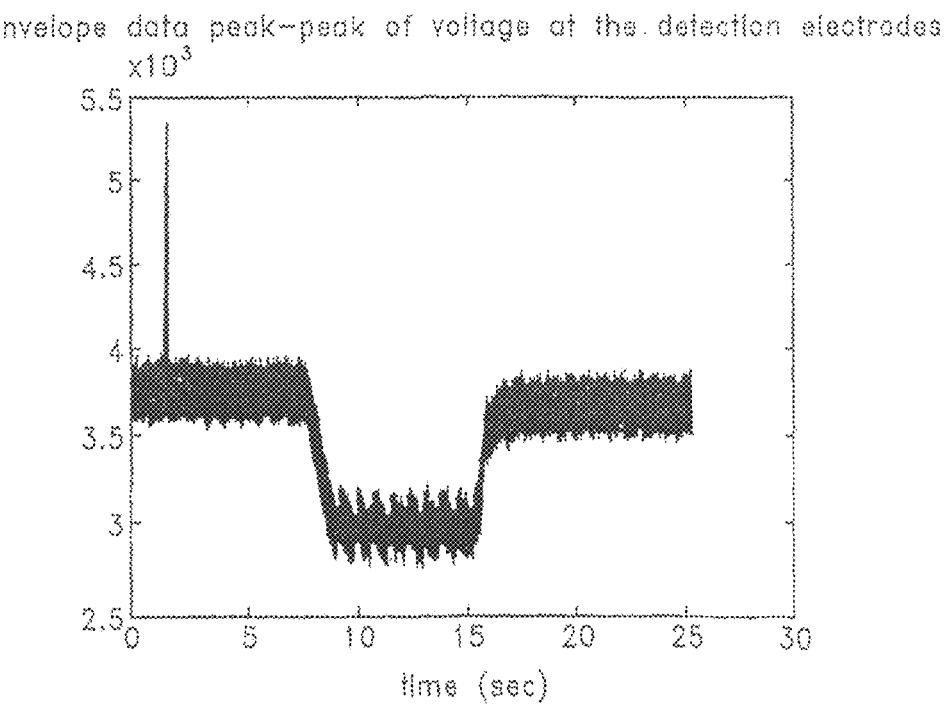
FIG. 4B shows the peak-to-peak envelope of the detected voltage shown in FIG. 4A, according to an embodiment of the present disclosure.
Figure 5A:
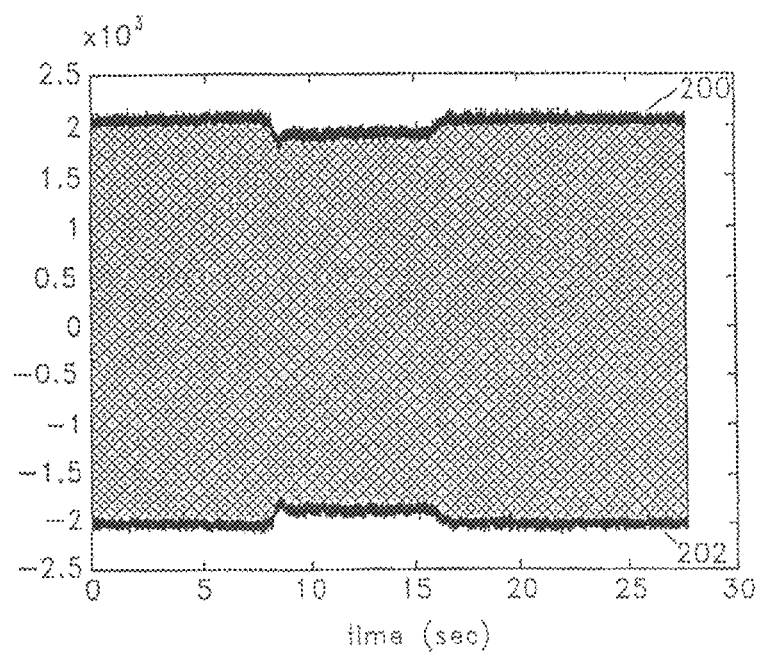
FIG. 5A shows the detected filtered voltage drop as measured in the blood stream before and after injection of 0.5% NaCl solution, according to an embodiment of the present disclosure.
Figure 5B:
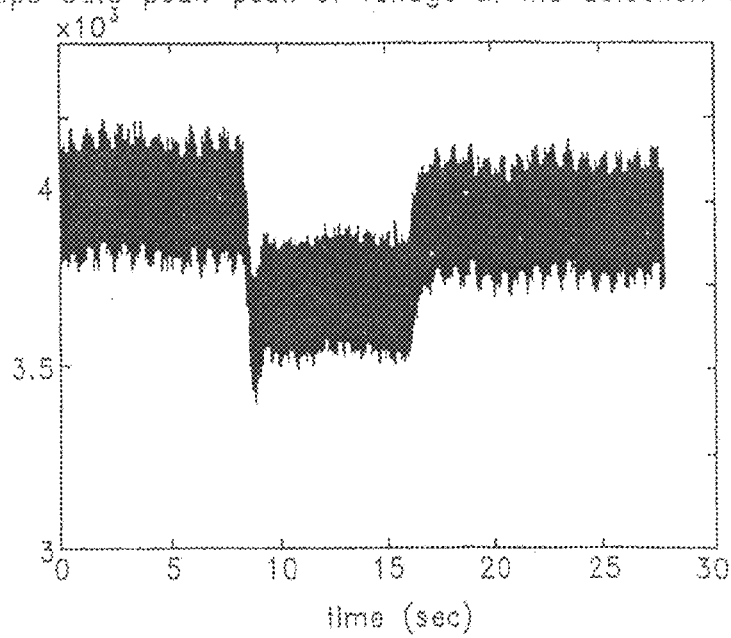
FIG. 5B shows the peak-to-peak envelope of the detected voltage shown in FIG. 5A, according to an embodiment of the present disclosure.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation [4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 mm² (3 mm in diameter) to 1017 mm² (36 in mm). If the conductivity of the solutions is obtained from a conductivity meter independent of the catheter, however, then the CSA of the catheter is generally added to the CSA computed from Equation [4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the CSA.

Figure 6:
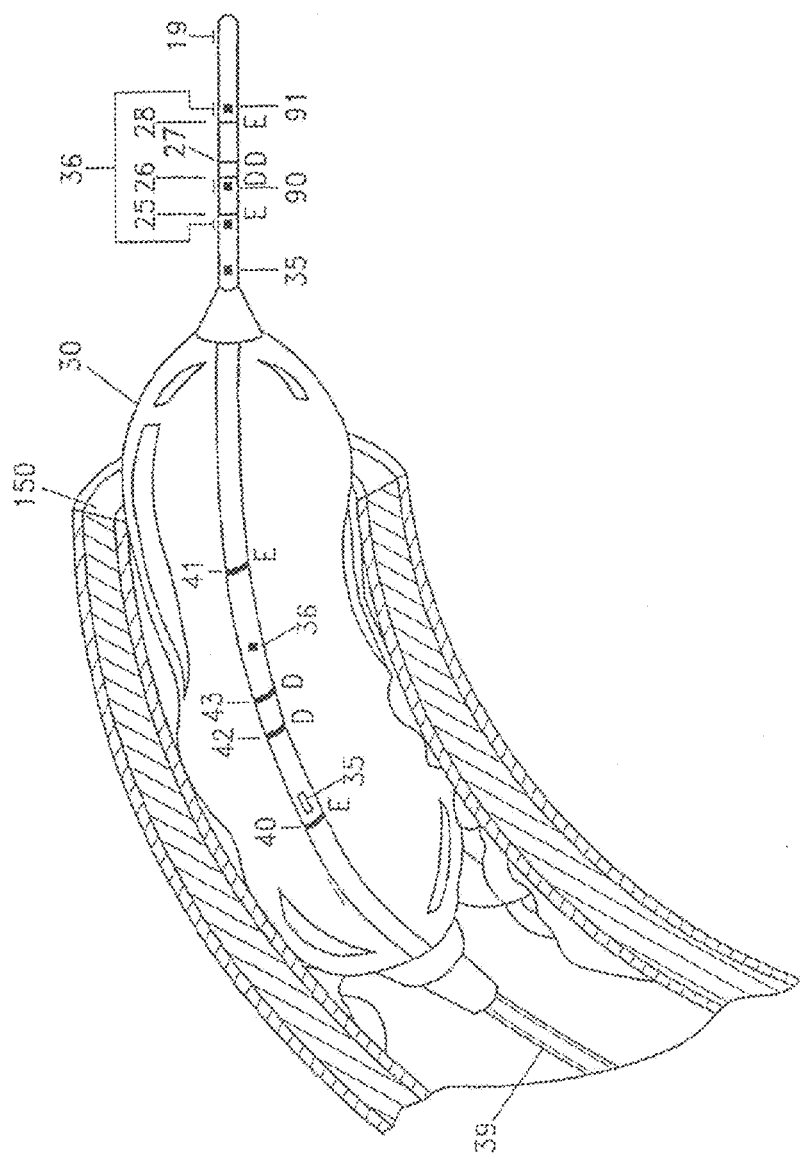
FIG. 6 shows balloon distension of the lumen of the coronary artery, according to an embodiment of the present disclosure.
Figure 7A:
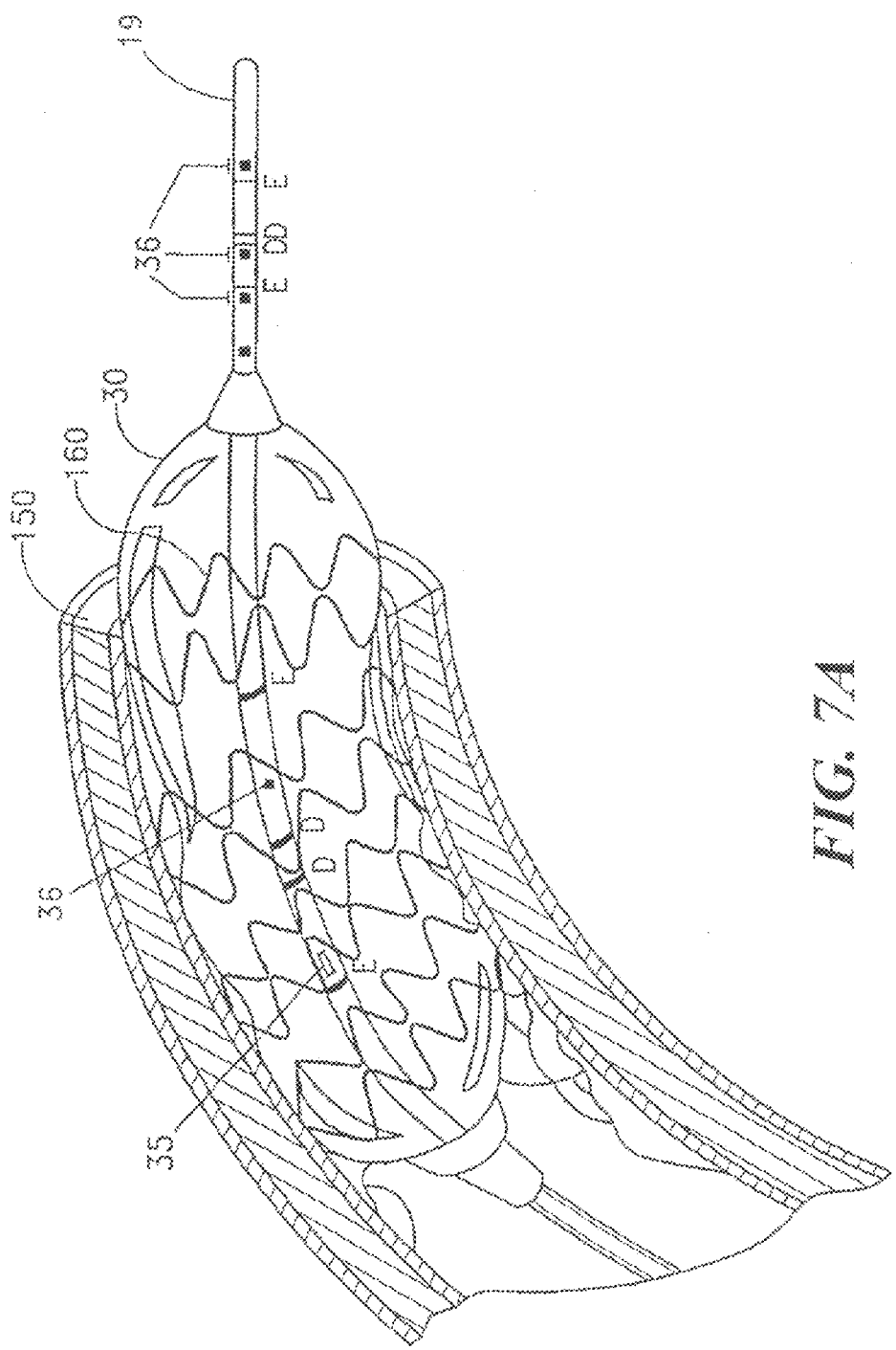
FIG. 7A shows balloon distension of a stent into the lumen of the coronary artery, according to an embodiment of the present disclosure.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7A, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stenosis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogential tract.

Finite Element Analysis:

In one preferred approach, finite element analysis (FEA) is used to verify the validity of Equations [4] and [5]. There are two major considerations for the model definition: geometry and electrical properties. The general Equation governing the electric scalar potential distribution, V, is given by Poisson's Equation as:

$$\nabla \cdot (C \nabla V) = -I \quad [13]$$

where C, I and $\nabla$ are the conductivity, the driving current density and the del operator, respectively. Femlab or any standard finite element packages can be used to compute the nodal voltages using Equation [13]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; i.e., minimize the non-homogeneity of the field. Furthermore, we simulated the experimental procedure by injection of the two solutions of NaCl to verify the accuracy of Equation [4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

We solved the Poisson's Equation for the potential field which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Figure 7B:
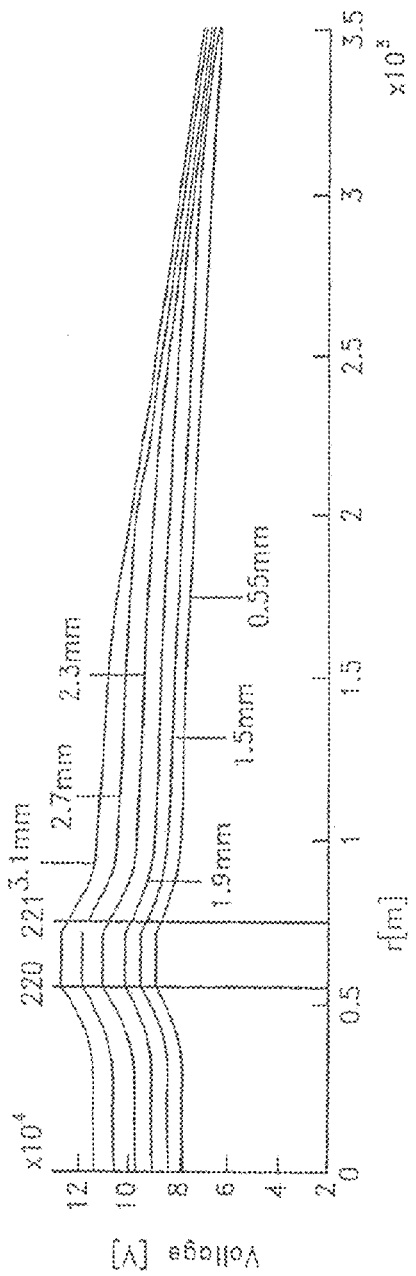
FIG. 7B shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site, according to an embodiment of the present disclosure.
Figure 7C:
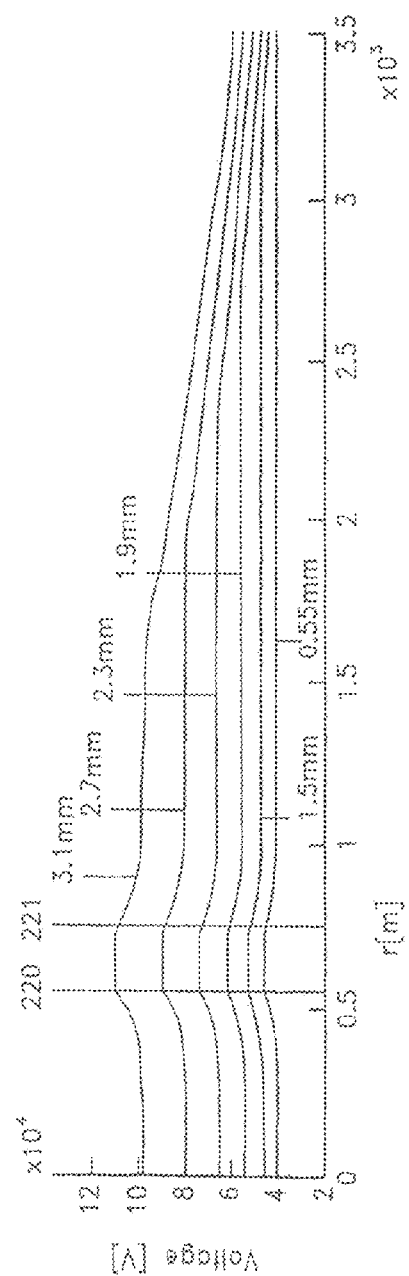
FIG. 7C shows the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site, according to an embodiment of the present disclosure.

Theoretically, it is impossible to ensure a completely homogeneous field given the current leakage through the vessel wall into the surrounding tissue. We found that the iso-potential line is not constant as we move out radially along the vessel as stipulated by the cylindrical model. In one embodiment, we consider a catheter with a radius of 0.55 mm whose detected voltage is shown in FIGS. 7B and 7C for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5 and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, our simulation generates the "hill" whose value corresponds to the equivalent potential in the vessel as used in Equation [4]. Hence, for each catheter size, we varied the dimension of the vessel such that Equation [4] is exactly satisfied. Consequently, we obtained the optimum catheter size for a given vessel diameter such that the distributive model satisfies the lumped Equations (Equation [4] and [5]). In this way, we can generate a relationship between vessel diameter and catheter diameter such that the error in the CSA measurement is less than 5%. In one embodiment, different diameter catheters are prepackaged and labeled for optimal use in certain size vessel. For example, for vessel dimension in the range of 4-5 mm, 5-7 mm or 7-10 mm, our analysis shows that the optimum diameter catheters will be in the range of 0.9 1.4, 1.4-2 or 2-4.6 mm, respectively. The clinician can select the appropriate diameter catheter based on the estimated vessel diameter of interest. This decision will be made prior to the procedure and will serve to minimize the error in the determination of lumen CSA.

The present disclosure also includes disclosure of impedance devices and systems having particular electrode spacing, which is used to obtain optimal conductance and/or fluid velocity measurements, as well as devices and systems having a new and unique arrangements of electrodes to facilitate optimal conductance and fluid velocity measurements.

Various devices and systems of the present disclosure having a tetrapolar arrangement of electrodes 25, 26, 27, 28, as shown in FIGS. 1A, 1B, and 1E, for example, may have a particular spacing of electrodes so to facilitate optimal conductance measurements. As referenced above, and in at least one exemplary embodiment, electrodes 26 and 28 are spaced 1 mm apart and form the inner (detection) electrodes, and electrodes 25 and 27 are spaced 4-5 mm from either side of the inner electrodes and form the outer (excitation) electrodes. In at least one specific example, the electrodes have a 4-1-4 spacing arrangement, which is indicative of the spacing (in millimeters) between electrodes 25, 26, 27, 28. For example, and as shown in FIG. 1E, the electrodes, starting from the most distal electrode, are in order of 27, 28, 26, and 25. With the 4-1-4 arrangement (most distal first), at least one exemplary device embodiment of the present disclosure has an electrode spacing of or about 4 mm between electrodes 25 and 26, of or about 1 mm between electrodes 26 and 28, and or of about 4 mm between electrodes 28 and 27. Such a spatial arrangement about a wire embodiment, as shown in FIG. 1E for example, or a catheter embodiment, as shown in FIGS. 1A-1D for example, may be optimal for obtaining conductance (and eventual sizing) measurements within relatively small luminal organs.

Such embodiments, as shown in FIGS. 1A-1E, are referred to tetrapolar embodiments as they each comprise four electrodes in a tetrapolar arrangement (outside of a balloon 30) to facilitate sizing measurements within luminal organs. However, the addition of a fifth electrode, specifically and uniquely placed most proximal to the tetrapolar electrodes, can allow for optimal fluid velocity measurements in addition to sizing measurements as referenced herein. Embodiments of devices and systems of the present disclosure having a five-electrode arrangement, as provided in further detail below, are referred to herein as "pentapolar" embodiments.

An exemplary device of the present disclosure having a pentapolar arrangement of electrodes, and therefore capable of obtaining optimal sizing measurements as well as optimal fluid velocity measurements due to their unique and particular arrangement and operation of electrodes, is shown in FIG. 8A. As shown in FIG. 8A, an exemplary device 300, which may have one or more features of various other devices and systems of the present disclosure, such as catheter 20 shown in FIG. 1A, catheter 39 shown in FIG. 1B, catheter 21 shown in FIG. 1C, catheter 22 shown in FIG. 22, and wire 18 shown in FIG. 1E, for example, comprises an elongated body 302 with various electrodes positioned thereon or therein. Body 302, in various embodiments, may comprise various wires or catheters useful in the medical arts that are configured with an exemplary unique arrangement of electrodes as referenced herein.

As shown in FIG. 8A, an exemplary device 300 of the present comprises five electrodes, namely electrodes 304 (corresponding to electrode "A"), 306 (corresponding to electrode "B"), 308 (corresponding to electrode "C"), 310 (corresponding to electrode "D"), and 312 (corresponding to electrode "E"). Such electrodes, as shown in FIGS. 8A and 8B, may be referred to as a detector 314, whereby detector 314 is operable to obtain sizing measurements as well as fluid velocity measurements. In at least one embodiment, the electrodes of device 300 have a 4-1-4-8 spacing arrangement, which is indicative of the spacing (in millimeters) between electrodes 304, 306, 308, 310, 312. For example, and as shown in FIG. 8A, the electrodes, starting from the most distal electrode, are in order of 304, 306, 308, 310, and 312. With the 4-1-4-8 arrangement (most distal first), at least one exemplary device 300 embodiment of the present disclosure has an electrode spacing of or about 4 mm between electrodes 304 and 306, of or about 1 mm between electrodes 306 and 308, of or about 4 mm between electrodes 308 and 310, and of or about 8 mm between electrodes 310 and 312. This spacing is in reference to at least one embodiment of a device 300 of the present disclosure, noting that said spacing is not arbitrary given the special considerations relating to impedance, as an arbitrary electrode spacing would likely result in a device that either can only obtain conductance measurements with a very high error percentage, or result in a device that cannot effectively obtain a conductance measurement regardless of error.

With respect to electrode 312 in particular, it is noted that in the above-referenced embodiment, electrode 312 is spaced furthest away from its adjacent electrode, namely electrode 310, than any other electrode spacing upon device 300. Such spacing allows an exemplary device 300 of the present disclosure to not only obtain optimal sizing measurements, but optimal velocity measurements as well.

The device 300 embodiment shown in FIG. 8A, and the exemplary catheter and wire embodiments shown in FIGS. 1A-1E, for example, can be used to obtain sizing measurements in a similar fashion. For example, and regarding a device 300 embodiment having a pentapolar arrangement of electrodes, the four most distal electrodes can be used to obtain sizing measurements similar to a device having a tetrapolar arrangement of electrodes. For example, an exemplary device 300 embodiment, such as shown in FIG. 8A, can be used to obtain a sizing measurement within a luminal organ by way of exciting using electrodes A and D (namely electrodes 304 and 310) and detecting using electrodes B and C (namely electrodes 306 and 308), similar to the excitation of electrodes 25 and 27 and the detection using electrodes 26 and 28 as generally referenced herein with respect to various device and system embodiments.

Such a tetrapolar arrangement could also be used to obtain fluid velocity measurements, but there is a clear compromise with respect to spacing and accuracy of the sizing and velocity measurements when using a tetrapolar arrangement of electrodes. For example, one would desire to have the inner detection electrodes (namely electrodes 26 and 28 as shown in FIG. 1A, for example, or electrodes B and C (namely electrodes 306 and 308) as shown in FIG. 8A) be relatively close together to obtain optimal sizing measurements. However, and if using a tetrapolar arrangement of electrodes to measure velocity, one would use electrodes 27 and 28 together and would also use electrodes 25 and 26 together, so that 27&28 and 25&26 act as the two detectors, separated by a distance, to obtain velocity measurements. However, when electrodes 26 and 28 are relatively close together, the effective distance between the two velocity detectors (namely 27&28 and 25&26) is very small, leading to relatively inaccurate or unreliable velocity measurements. If the inner electrodes (electrodes 26 and 28) are spaced further apart so to obtain a more accurate and reliable velocity measurement, the accuracy and reliability of the sizing measurements decreases as the distance between the inner electrodes (used as detectors for sizing) increases past 1 mm, for example.

To overcome this inherent compromise, the present disclosure provides for various devices 300 having a pentapolar arrangement so that four of the five electrodes can be used to obtain optimal sizing measurements, and a different four of the five electrodes can be used to obtain optimal fluid velocity measurements. For example, and using device 300 as shown in FIG. 8A as an example, device 300 could be used to obtain sizing measurements by exciting electrodes A and D and detecting using electrodes B and C. Device 300 could also then be used to obtain velocity measurements by exciting electrodes A and E and by detecting using electrodes A&B and electrodes C&E.

The exemplary 4-1-4-8 configuration referenced herein is an exemplary configuration optimized for sizing and fluid velocity measurements within mammalian luminal organs whereby sizing (such as sizing to identify an appropriately-sized stent, for example) is relatively common. However, for larger luminal organs, a different configuration may be required so that the electrode spacing is sufficient to obtain, for example, a luminal cross-sectional area measurement for a luminal organ larger than a typical mammalian artery, for example. As referenced in at least one embodiment herein, the 4-1-4-8 arrangement correspond to spacings of 4 mm, 1 mm, 4 mm, and 8 mm, and in other embodiments, the 4-1-4-8 arrangement may be indicative of a spacing ratio different than the corresponding millimeters.

Another exemplary embodiment of a device 300 of the present disclosure is shown in FIG. 8B. As shown in FIG. 8B, an exemplary device 300 comprises a body 302 and a balloon 30 positioned thereon proximal to detector 314 so that any gas and/or fluid injected through body 302 into balloon 30 by way of a suction/infusion port 35 will not leak into a patient's body when such a device 300 is positioned therein.

As shown in FIG. 8B, device 500 comprises a second detector 316, wherein detector 316, in at least one embodiment, comprises a tetrapolar arrangement of two excitation electrodes 40, 41 and two detection electrodes 42, 43 located inside balloon 30 for accurate determination of the balloon 30 cross-sectional area during sizing of a valve annulus. Such a tetrapolar arrangement of electrodes (excitation, detection, detection, and excitation, in that order) as shown in FIG. 8B would allow sizing within balloon 30, including the determination of balloon 30 cross-sectional area at various stages of inflation.

As shown in FIG. 8B, device 300 may comprise a catheter (an exemplary body 300), wherein balloon 30 is positioned thereon. In addition, an exemplary embodiment of a device 300, as shown in FIG. 8B, comprises a pressure transducer 48 capable of measuring the pressure of a gas and/or a liquid present within balloon 30. Device 300, in at least one embodiment as referenced herein, also has a suction/infusion port 35 defined within catheter 39 inside balloon 30, whereby suction/infusion port 35 permits the injection of a gas and/or a fluid from a lumen of catheter 39 into balloon 30, and further permits the removal of a gas and/or a fluid from balloon 30 back into catheter 39.

The exemplary embodiments of devices 300 shown in FIGS. 8A and 8B are not intended to be the sole embodiments of said devices 300, as various devices 300 of the present disclosure may comprise additional components as shown in various other figures and described herein. For example, an exemplary system of the present disclosure may comprise a device 300 coupled to one more components shown in FIG. 3 just as catheter 20 shown therein is coupled thereto.

At least one embodiment of an exemplary device 300 of the present disclosure is shown in FIG. 9A. As shown in FIG. 9A, electrodes A, B, C, and D (numbered as electrodes 304, 306, 308, and 310 in the figure) are shown in a 4-1-4 tetrapolar arrangement. The numbers appearing below device 300 in the FIG. 9A represent the spacing between electrodes in millimeters and also identify an approximate 1 mm width of each electrode.

The distance between excitation electrodes would be at least two times (2×) the diameter of the vessel being sized. For example, in a 4-1-4 tetrapolar arrangement of electrodes, and considering that each exemplary electrode itself is approximately 1 mm in diameter, the distance between the two excitation electrodes (electrodes 304 and 310) is 11 mm. This calculation is identified by way of the measurements shown in FIG. 9A, whereby each electrode is shown as having a 1 mm length, and whereby the electrodes are shown in a 4-1-4 tetrapolar arrangement (namely 4 mm, 1 mm, and 4 mm from one another). With such an arrangement and size, vessels of up to about 5 mm in diameter (such as coronary vessels) can be measured, as the distance between excitation electrodes (11 mm) is at least two times the diameter (up to about 5 mm) being measured.

Peripheral vessels, having diameters as large as 10 mm in some instances, would require a different electrode spacing than a 4-1-4 arrangement, as such an arrangement would not obtain accurate measurements within a vessel of that size. For example, if a device 300 having a 4-1-4 tetrapolar arrangement of electrodes were used to size a vessel having a 10 mm diameter, the electric field would form a relative sphere instead of a relative cylindrical shape, resulting in an inaccurate impedance measurement.

Accordingly, an exemplary device 300 of the present disclosure configured to size peripheral vessels is shown in FIG. 9B. As shown in FIG. 9B, electrodes A, B, C, and D (numbered as electrodes 304, 306, 308, and 310 in the figure) are shown in a 5-2-10 tetrapolar arrangement. The numbers appearing below device 300 in the FIG. 9B represent the spacing between electrodes in millimeters and also identify an approximate 1 mm width of each electrode. As shown in FIG. 9B, device 300 has a 5-2-10 tetrapolar arrangement of electrodes, whereby the most distal electrode (electrode 304) is 5 mm from its adjacent detection electrode (electrode 306), the two detection electrodes (electrodes 306 and 308) are 2 mm from one another, and the more proximal detection electrode (electrode 308) is 10 mm from the proximal excitation electrode (electrode 310). In such an arrangement, the distance between the two excitation electrodes 304, 310 is 19 mm, which is calculated by estimating the width of each electrode as 1 mm and adding the 5 mm, 2 mm, and 1 mm spacing to the two detection electrodes 306, 308. With such an arrangement and size, vessels of up to about 9 mm or 10 mm in diameter can be precisely measured.

In general, the further apart the excitation electrodes are positioned from one another, the greater the overall parallel conductance, meaning that more current is lost through the vessel itself. Because of this loss, injected current has a fraction within the lumen and a fraction within the surrounding tissue. Given the separation of excitation electrodes, and to get a proper signal to noise ratio, the detection electrodes are expanded from 1 mm to 2 mm in the 5-2-10 electrode arrangement.

Referring back to coronary vessel sizing (up to about 5 mm in diameter), and as referenced generally above, it is preferred to add a fifth electrode to the tetrapolar arrangement to obtain velocity measurements and effectively decouple sizing from velocity. However, and in attempts to optimize a tetrapolar arrangement of electrodes useful for accurate sizing and velocity measurements, a 3-1-6 tetrapolar arrangement was attempted (instead of 4-1-4), and such an arrangement was not successful in obtaining accurate impedance measurements. However, when a 3-2-6 arrangement was tried, it was successfully able to obtain sizing and velocity measurements.

Figure 10A:
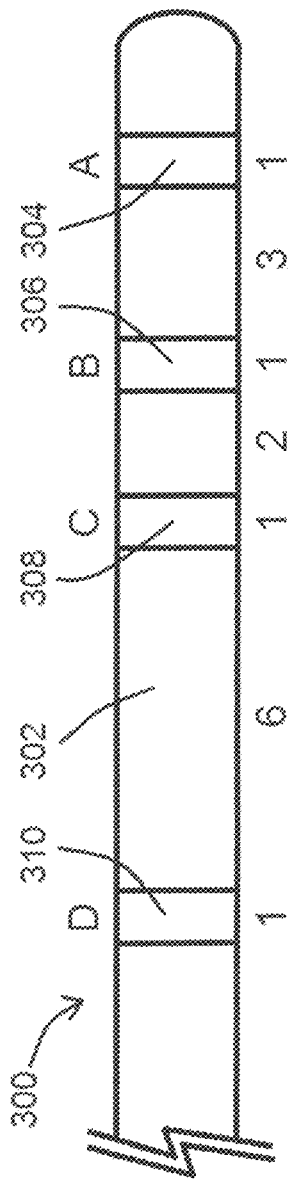

Another exemplary embodiment of an exemplary device 300 of the present disclosure is shown in FIG. 10A. As shown in FIG. 10A, electrodes A, B, C, and D (numbered as electrodes 304, 306, 308, and 310 in the figure) are shown in a 3-2-6 tetrapolar arrangement. The numbers appearing below device 300 in the FIG. 10A also represent the spacing between electrodes in millimeters, and also identify an approximate 1 mm width of each electrode.

With a 3-2-6 arrangement, for example, velocity measurements may be obtained by measuring using the two distal electrodes (electrodes 304 and 306, 3 mm apart) and the two proximal electrodes (electrodes 308 and 310, 6 mm apart). When a constant voltage is applied to the vessel, a voltage drop would be indicative of a first deflection (the two proximal electrodes) and a second deflection (the two distal electrodes) as a bolus of fluid passes across the electrodes. As the first deflection would be identified when the bolus hits the most proximal electrode (namely electrode D) and the second deflection would be identified when the bolus passes the electrode just proximal to the most distal electrode (namely electrode B), the bolus would pass 9 mm after passing electrode D before passing electrode B, resulting in an accurate velocity determination.

An exemplary device having a 4-1-4-8 pentapolar arrangement of electrodes, as referenced above, would allow a bolus to travel 15 mm between the two trigger velocity measurements. For example, velocity measurements could be obtained in a 4-1-4-8 arrangement by exciting electrodes A and E and by detecting using electrodes A&B and electrodes C&E, as referenced above. The two triggers would be at electrode E and electrode B, so that the bolus would pass 8 mm (the distance between electrodes E and D) plus 1 mm (the size of electrode D) plus 4 mm (the distance between electrodes D and C) plus 1 mm (the size of electrode C) plus 1 mm (the distance between electrodes C and B), for a total of 15 mm. As such, the use of a fifth electrode (electrode E) for velocity measurements effectively decouples the sizing and velocity measurements in a 4-1-4-8 embodiment, and if there is no fifth electrode, a 3-2-6 tetrapolar arrangement of electrodes could be used.

Accordingly, and as referenced above, an exemplary device 300 of the present disclosure comprises an elongated body 302 and a detector 314 positioned upon elongated body 302, wherein detector 302 comprises at least five electrodes and configured to obtain one or more conductance measurements generated using a first arrangement of four of the at least five electrodes and further configured to obtain one or more fluid velocity measurements using a second arrangement of four of the at least five electrodes when elongated body 302 is positioned within a fluid environment of a mammalian luminal organ, wherein the first arrangement is different from the second arrangement. Such an exemplary device may comprise a wire and a catheter having the aforementioned features.

In at least one embodiment, at least three electrodes of the at least five electrodes are capable of excitation to generate an electric field when a current source capable of supplying electrical current to the at least three electrodes is operably coupled thereto, and at least two electrodes of the at least five electrodes are capable of are capable of obtaining one or more luminal organ measurements selected from the group consisting of the one or more conductance measurements and the one or more fluid velocity measurements. In various embodiments, when the at least two electrodes are operably connected to a data acquisition and processing system, the data acquisition and processing system is capable of receiving the one or more luminal organ measurements and calculating a cross-sectional area of the luminal organ based in part upon the one or more luminal organ measurements and a known distance between the at least two electrodes.

With respect to an exemplary device 300 of the present disclosure having five electrodes and not more than five electrodes (which can occur as provided in detail below), said electrodes comprise a most distal electrode (electrode 304), an electrode immediately adjacent to the most distal electrode (electrode 306), a most proximal electrode (electrode 312), an electrode immediately adjacent to the most proximal electrode (electrode 310), and a central electrode positioned between the electrode immediately adjacent to the most distal electrode and the electrode immediately adjacent to the most proximal electrode (electrode 308). In at least one embodiment, the first arrangement of electrodes comprises the most distal electrode (electrode 304), the electrode immediately adjacent to the most distal electrode (electrode 306), the central electrode (electrode 308), and the electrode immediately adjacent to the most proximal electrode (electrode 310), wherein electrode 304 and electrode 310 are capable of excitation to generate an electric field, and wherein electrode 306 and electrode 308 are configured to obtain the one or more conductance measurements within the electric field. In various embodiments, one or more cross-sectional areas can be calculated based in part upon the one or more conductance measurements and a known distance between electrode 306 and electrode 308.

In at least one embodiment of a device 300 of the present disclosure, when body 302 is positioned within a fluid environment of a mammalian luminal organ and wherein when the fluid environment includes an indicator, the most proximal electrode (electrode 312) is operable to detect the indicator, and detection of the indicator facilitates activation of the first arrangement of electrodes so that the first arrangement of electrodes can obtain the one or more conductance measurements within the electric field.

In various embodiments, the second arrangement of electrodes comprises the most distal electrode (electrode 304), the electrode immediately adjacent to the most distal electrode (electrode 306), the central electrode (electrode 308), and the most proximal electrode (electrode 312), wherein electrode 304 and electrode 312 are capable of excitation to generate an electric field, wherein electrode 304 and electrode 306 comprise a first fluid velocity detection electrode pair, and wherein electrode 308 and electrode 312 comprise a second fluid velocity detection pair. In such an embodiment, for example, body 302 is positioned within the fluid environment and wherein the fluid environment comprises an indicator, movement of the indicator past the first fluid velocity detection electrode pair (electrode 304, 306) and the second fluid velocity detection electrode pair (electrodes 308, 312) allows the first fluid velocity detection electrode pair and the second fluid velocity detection electrode pair to obtain the one or more fluid velocity measurements. As referenced herein, the term "indicator" is intended to include a substance or property within a fluid that can be detected by an electrode, such as a salt, a dye, a specific chemical, etc., and is not intended to be limited to any particular detectable substance or property.

Figure 10B:
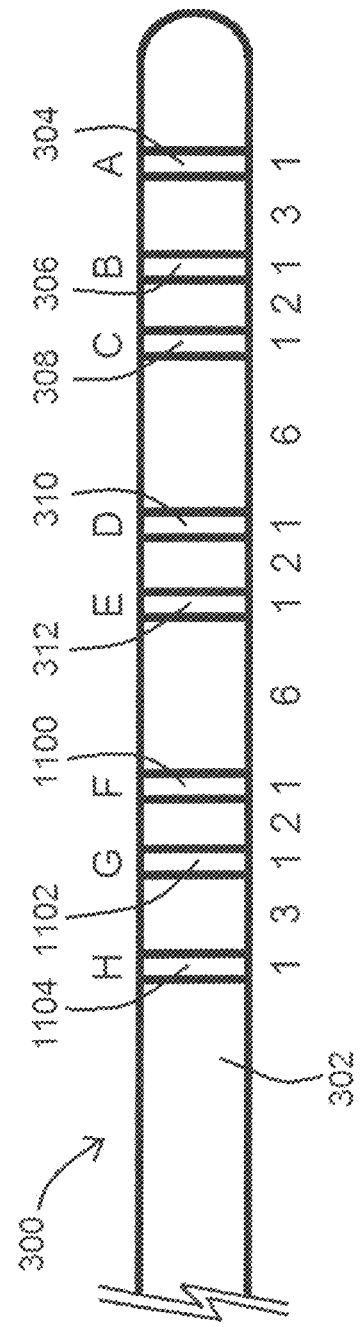

Another exemplary embodiment of a device 300 of the present disclosure is shown in FIG. 10B. As shown in FIG. 10B, an octapolar arrangement of electrodes having a 3-2-6-2-6-2-3 spacing arrangement is shown, whereby device 300 is operable to simultaneously obtain three cross-sectional area measurements. In such an embodiment, device 300 could be used to, for example, obtain cross-sectional areas within a vessel proximal to a stenosis, at a stenosis, and distal to a stenosis.

FIG. 10B shows electrodes 304, 306, 308, 310, and 312 (corresponding to electrodes A, B, C, D, and E, respectively) and three additional electrodes 1100, 1102, and 1104 (corresponding to electrodes F, G, and H, respectively), whereby electrodes A-H are in alphabetical order starting from the distal end of device 300 (electrode A) and moving toward the proximal end of device 300 (electrode H). The numbers appearing below device 300 in the FIG. 10B also represent the spacing between electrodes in millimeters, and also identify an approximate 1 mm width of each electrode.

In such an embodiment, a distal sizing measurement can be obtained by exciting electrodes A and D (13 mm apart) and detecting with electrodes B and C (2 mm apart), a central sizing measurement can be obtained by exciting electrodes C and F (16 mm apart) and detecting with electrodes D and E (2 mm apart), and a proximal sizing measurement can be obtained by exciting electrodes E and H (13 mm apart) and detecting with electrodes F and G (2 mm apart). If device 300 is then moved to a different position within the luminal organ, three additional sizing measurements can be obtained simultaneously.

Velocity measurements can also be made using a device 300 having a 3-2-6-2-6-2-3 octapolar spacing arrangement as shown in FIG. 10B. With such an electrode arrangement, for example, velocity measurements may be obtained by exciting with electrodes A and H and measuring using electrodes H and D (electrodes 1104 and 310), providing a 13 mm-15 mm distance between the two deflections to provide an accurate velocity measurement. As referenced above, when a constant voltage is applied to the vessel, a voltage drop would be indicative of a first deflection (the two proximal electrodes) and a second deflection (the two distal electrodes) as a bolus of fluid passes across the electrodes. As the first deflection would be identified when the bolus hits the most proximal electrode (namely electrode H) and the second deflection would be identified when the bolus passes electrode D, resulting in an accurate velocity determination given the spacing between electrodes D and H.

In use, and as referenced above, exemplary devices 300 can be introduced into a luminal organ, and using one or more fluid injections, devices 300 can be used to obtain conductance measurements (useful to determine cross-sectional areas, for example), and also used to determine fluid velocity using the electrode arrangements referenced above.

In such an octapolar electrode arrangement, such as shown in FIG. 10B, the eight electrodes comprise a most distal electrode (electrode 304), an electrode immediately adjacent to the most distal electrode (electrode 306), a most proximal electrode (electrode 1104), an electrode immediately adjacent to the most proximal electrode (electrode 1102), a central distal electrode (electrode 310), a central proximal electrode (electrode 312), an electrode immediately adjacent to and distal to the central distal electrode (electrode 308), and an electrode immediately adjacent to and proximal to the central proximal electrode (electrode 1100). In such an embodiment, the most distal electrode (electrode 304) and the central distal electrode (electrode 310) are capable of excitation to generate a distal electric field, wherein the electrode immediately adjacent to and distal to the central distal electrode (electrode 308) and the electrode immediately adjacent to and proximal to the central proximal electrode (electrode 1100) are capable of excitation to generate a central electric field, wherein the central proximal electrode (electrode 312) and the most proximal electrode (electrode 1104) are capable of excitation to generate a proximal electric field, wherein the one or more conductance measurements can be obtained within each of the distal electric field, the central electric field, and the proximal electric field, and wherein one or more cross-sectional areas can be calculated based in part upon the one or more conductance measurements and known distances between the electrodes used to generate the distal electric field, the central electric field, and the proximal electric field.

In various octapolar device 300 embodiments, the second arrangement of electrodes comprises the most distal electrode, the central distal electrode, the central proximal electrode, and the most proximal electrode, wherein the most distal electrode and the central distal electrode comprise a first fluid velocity detection electrode pair, and wherein the central proximal electrode and the most proximal electrode comprise a second fluid velocity detection pair. In at least one embodiment, when the elongated body is positioned within the fluid environment and wherein the fluid environment comprises an indicator, movement of the indicator past the first fluid velocity detection electrode pair and the second fluid velocity detection electrode pair allows the first fluid velocity detection electrode pair and the second fluid velocity detection electrode pair to obtain the one or more fluid velocity measurements.

The present disclosure also includes disclosure of methods of obtaining conductance and/or conductivity measurements useful to facilitate obtaining reliable luminal organ size measurements/parameters in connection with injection(s) of a single concentration of fluid. For example, various devices of the present disclosure may be used in connection with injections of a single concentration of saline to reliably obtain mammalian luminal organ cross-sectional areas, diameters, and/or radii at locations within the mammalian luminal organ with and without a stenosis.

An exemplary device of the present disclosure useful to perform said methods is shown in FIG. 11A. As shown therein, a device 1150, which may be one of an impedance catheter 20 (shown in FIG. 1A), an impedance catheter 39 (shown in FIG. 1B), an impedance catheter 21 (shown in FIG. 1C), an impedance catheter 22 (shown in FIG. 1D), an impedance wire 18 (shown in FIG. 1E), an impedance catheter (as shown in FIG. 1F), an impedance device 300 (as shown in one or more of FIGS. 8A-10B), or another impedance device having one or more components of the present disclosure thereon sufficient to obtain desired conductance measurements, which may then be useful to ultimately determine the mammalian luminal organ geometry of interest. For example, an exemplary device 1150, as shown in FIG. 11A, comprises an elongated body 302 having a detector 314 comprising a tetrapolar arrangement of two detection electrodes (electrodes 306 ("B") and 308 ("C")) positioned in between two excitation electrodes (electrodes 304 ("A") and 310 ("D")). An exemplary detector 314, as referenced herein, may have additional electrodes/sensors as well, such as electrode 312 ("E"), as shown in FIG. 8A, and/or electrodes 1100 ("F"), 1102 ("G"), and 1104 ("H"), as shown in FIG. 10B. Furthermore, and as shown in FIG. 11A, device 1150 may comprise one or more temperature sensors 1152 (which may be one or more thermistors operable to obtain temperature data), that may use one or more wires (not shown) for ultimate operation to detect temperature.

Exemplary devices 1150, in at least a few embodiments of the present disclosure and for use in connection with a number of methods as referenced herein, would be at least partially surrounded by an outer sheath 1175. Outer sheath 1175, in various embodiments, may be guide catheters or non-catheter sheaths having at least one lumen 1180 defined therethrough. Lumen 1180 would be sized and shaped to receive at least portions of devices 1150 therethrough, and outer sheath 1175 itself would sized and shaped to fit within one or more mammalian luminal organs of interest. For example, device 1150 may be an impedance wire 18 as shown in FIG. 1E, or any number of the device 1150 embodiments of the present disclosure, and may be at least partially surrounded by an outer sheath 1175, which may be a guide catheter 23 also shown in FIG. 1E. Electrodes 25, 26, 27, and 28, as shown in FIG. 1E, could be the same electrodes as electrodes 310, 308, 306, and 304, respectively, as shown in FIGS. 8A and 11.

FIG. 11A shows an exemplary device 1150 of the present disclosure at least partially surrounded by an outer sheath 1175 so that the detector 314 of device 1150 is exposed (not positioned within the lumen 1180 of outer sheath 1175). By moving device 1150 relative to outer sheath 1175, by withdrawing device 1150, or by advancing outer sheath 1175 along device 1150, detector 314 can be surrounded by outer sheath 1175, as shown in FIG. 11B, allowing device 1150 to be used to obtain conductance measurements within outer sheath 1175 as described in detail below.

As mentioned above, exemplary devices 1150 of the present disclosure can be used to ultimately obtain luminal organ geometries (cross-sectional areas, diameters, etc.) by injecting only one concentration of a fluid. In at least one exemplary embodiment of a method for obtaining one or more conductance measurements using a device 1150 of the present disclosure, the method 1200, as shown by the method steps in FIG. 12, comprises the steps of introducing at least part of an impedance device 1150 into a mammalian luminal organ, the impedance device 1150 comprising an elongated body 302 and a detector 314 positioned along elongated body 314 (an exemplary introduction step 1202), and obtaining a first conductance measurement using detector 314 while detector 314 is surrounded by an outer sheath 1175 surrounding at least part of impedance device 1150, and wherein the first conductance measurement is indicative of a fluid native to the mammalian luminal organ (such as blood, for example) present within a lumen 1180 of outer sheath 1175 (an exemplary first conductance measurement step 1204). The first conductance measurement (indicative of a native fluid, such as blood, for example, within outer sheath 1175) may be referred to herein as $g_{native}$ or $g_{blood}$ if the native fluid is blood, with the lowercase "g" referring to conductance within outer sheath 1175. As noted below, conductance outside of outer sheath 1175 may be referred to herein with an uppercase "G".

Method 1200, in at least one embodiment, further comprises the optional step of obtaining a second conductance measurement using detector 314 while detector 314 is surrounded by outer sheath 1175, wherein the second conductance measurement is indicative of a first injection of a first solution of a first compound (such as 0.90N saline, for example) through lumen 1180 of the outer sheath 1175 (an exemplary second conductance measurement step 1206). Various methods of the present disclosure may further comprise the steps of moving impedance device 1150 and/or outer sheath 1175 relative to one another so that outer sheath 1175 no longer surrounds 314 detector (an exemplary device movement step 1208), obtaining a third conductance measurement using detector 314, wherein the third conductance measurement is indicative of the fluid native to the mammalian luminal organ (an exemplary third conductance measurement step 1210), and obtaining a fourth conductance measurement using detector 314, wherein the fourth conductance measurement is indicative of a second injection of the first solution through lumen 1180 of outer sheath 1175 (an exemplary fourth conductance measurement step 1212). The second conductance measurement (indicative of an injected fluid, such as saline, for example, within outer sheath 1175) may be referred to herein as $g_{fluid}$ or $g_{saline}$ if the injected fluid is saline, for example. The third conductance measurement (indicative of a native fluid, such as blood, outside of outer sheath 1175) may be referred to herein as $G_{native}$ or $G_{blood}$ if the native fluid is blood, for example, with the uppercase "G" referring to conductance outside outer sheath 1175 (conductance with the luminal organ itself as a boundary). The fourth conductance measurement (indicative of an injected fluid, such as saline, for example, outside of outer sheath 1175) may be referred to herein as $G_{fluid}$ or $G_{saline}$ if the injected fluid is saline, for example. After obtaining the aforementioned conductance measurements, an exemplary method 1200 of the present disclosure comprises the step of calculating a size parameter of the mammalian luminal organ based in part upon the first conductance measurement ($g_{blood}$, if in the presence of blood), the second conductance measurement ($g_{saline}$, if in the presence of saline), the third conductance measurement ($G_{blood}$, if in the presence of blood), and the fourth conductance measurement ($G_{saline}$, if in the presence of saline) (an exemplary calculation step 1214).

In at least one embodiment of a method 1200 of the present disclosure, introduction step 1202 is performed using access through a patient's femoral artery and advancement of impedance device 1150 to a location of interest within the mammalian luminal organ. In various embodiments, first conductance measurement step 1204 is performed while an aperture 1185 defined within outer sheath 1175 (as shown in FIG. 11A) is opened to allow the fluid native to the mammalian luminal organ to flow within lumen 1180 of outer sheath 1175. Said aperture 1185 may be controlled using, for example, a valve 1190 (such as a stopcock, for example) as shown in FIG. 11B.

In exemplary embodiments of methods 1200 of the present disclosure, first conductance measurement step 1204 is performed while the fluid native to the mammalian luminal organ (such as blood, for example) is pulled into lumen 1180 of outer sheath 1175 using suction. In at least one embodiment, second conductance measurement step 1206 is performed when a desired temperature local to detector 314 is achieved, wherein the desired temperature indicative of the first injection of the first solution. The desired temperature may be determined, for example, by using a temperature sensor 1152 (such as a thermistor, for example), as shown in FIG. 11A, coupled to impedance device 1150 at or near detector 314, whereby temperature sensor 1152 is operable to detect temperature. An additional method may include, for example, performing second conductance measurement step 1206 when a threshold conductance is achieved, wherein the threshold conductance is indicative of a conductance sufficiently different from the first conductance measurement. For example, and to allow a user to determine whether or not second conductance measurement step 1206 is performed while the injected fluid is at detector 314, a notable/sizable change in conductance from the first conductance measurement can serve as a trigger.

In at least one embodiment of a method 1200 of the present disclosure, calculation step 1214 comprises calculating a conductivity of fluid native to the mammalian luminal organ (referred to herein as $\sigma_{native}$ or $\sigma_{blood}$ if the native fluid is blood) based in part upon the first conductance measurement ($g_{fluid}$ or $g_{saline}$) and the second conductance measurement ($g_{native}$ or $g_{blood}$). At least three different calculations are possible using, for example, the aforementioned conductances and the conductivity of the injected fluid ($\sigma_{fluid}$ or $\sigma_{saline}$) including the following (shown assuming the native fluid is blood and the injected fluid is saline):

(i) ratio method: $(g_{blood}/g_{saline}) \times \sigma_{saline} = \sigma_{blood}$     [14]

(ii) diameter method: $[(g_{blood}/(CSA_{OS}/L)] = \sigma_{blood}$     [15]

(iii) intercept method: $\sigma_{saline} - [(g_{saline} - g_{blood})/(CSA_{OS}/L)] = \sigma_{blood}$     [16]

wherein $CSA_{OS}$ is the known cross-sectional area of the inside of the outer sheath 1175, and wherein L is the known distance between detection electrodes 306, 308 of detector 314. Using any method referenced above in Equations [14] through [16], the conductivity of blood ($\sigma_{blood}$) can be determined.

In various method 1200 embodiments, methods 1200 further comprise the step of calibrating impedance device 1150 prior to performing introduction step 1202 (an exemplary calibration step 1216). Calibration step 1216, in various embodiments, can be performed by operating device 1150 within a plurality of phantoms of known sizes in the presence of the first solution to determine a conductivity of the first/injected fluid ($\sigma_{fluid}$ or $\sigma_{saline}$). For example, if multiple phantoms of different sizes are used, multiple conductance measurements can be made in the presence of the first fluid. Those conductance measurements can be plotted with the quotient of the phantom cross-sectional area and L on the x-axis and conductance on the y-axis, with the slope being indicative of the conductivity of the first/injected fluid ($\sigma_{fluid}$ or $\sigma_{saline}$).

Calculation step 1214, in various embodiments, can comprise calculating a conductivity of fluid native to the mammalian luminal organ ($\sigma_{native}$ or $\sigma_{blood}$ if the native fluid is blood) based upon the first conductance measurement, the second conductance measurement, and the conductivity of the first/injected fluid ($\sigma_{fluid}$ or $\sigma_{saline}$). Such a calculation may, for example, be performed using one or more of the ratio, diameter, and/or intercept methods shown in Equations [14] through [16] above.

In various embodiments, fourth conductance measurement step 1212 is performed when a desired temperature local to detector 314 is achieved, wherein the desired temperature indicative of the second injection of the first solution. Similar to an exemplary second conductance measurement step 1206, an exemplary fourth conductance measurement step 1212 can use temperature as a trigger when obtaining the conductance measurements. Temperature can serve as an effective trigger when the fluid injection (saline, for example) is at a lower temperature than blood temperature, so when the bolus of fluid passes over the temperature sensor 1152, a reduction in temperature can be detected, and a desired temperature and/or reduction in temperature can indicate a sufficient fluid bolus at detector 314, so that a dependable conductance measurement (in steps 1206 and/or 1212) can be made in the presence of the fluid bolus. In various embodiments, second conductance measurement step 1206, and/or fourth conductance measurement step 1212, can be performed by obtaining a plurality of conductance measurements over time.

Calculation step 1214, in at least one embodiment, may be further based in part upon a known distance between detection electrodes 306, 308 of detector 314. As referenced above, the distance L represents the known distance between detection electrodes 306, 308 of detector 314, and is a factor with the calculation to determine the conductivity of the first/injected fluid ($\sigma_{fluid}$ or $\sigma_{saline}$) in connection with device 1150 calibration (or to generally determine the said conductivity), and may also be a factor in connection with determining the conductivity of fluid native to the mammalian luminal organ ($\sigma_{native}$ or $\sigma_{blood}$ if the native fluid is blood) as shown in the diameter method (Equation [15]) and the intercept method (Equation [16]) referenced above.

In various method 1200 embodiments of the present disclosure, introducing step 1202 can be performed by introducing an impedance device 1150 selected from the group consisting of an impedance catheter and an impedance wire into the mammalian luminal organ, wherein impedance device 1150 is at least partially surrounded by an outer sheath 1175 selected from the group consisting of catheter and a non-catheter sheath.

In at least one exemplary embodiment of a method 1200 of the present disclosure, introduction step 1202 is performed by introducing the at least part of impedance device 1150 into the mammalian luminal organ at or near a stenosis, whereby impedance device 1150 can be used to perform one or more of the third conductance measurement step 1210 and/or the fourth conductance measurement step 1212 at or near the stenosis. In an exemplary embodiment, introduction step is performed by introducing the at least part of impedance device 1150 into the mammalian luminal organ at or near a stenosis, wherein method 1200 further comprises the steps of moving the at least part of the impedance device to a second location within the mammalian luminal organ (an exemplary second movement step 1218), obtaining a fifth conductance measurement using the detector 314, wherein the fifth conductance measurement is indicative of the fluid native to the mammalian luminal organ at the second location (an exemplary fifth conductance measurement step 1220), obtaining a sixth conductance measurement using detector 314, wherein the sixth conductance measurement is indicative of a third injection of the first solution through the lumen of outer sheath 1175 (an exemplary sixth conductance measurement step 1222), and calculating a second size parameter of the mammalian luminal organ at the second location based in part upon the first conductance measurement, the second conductance measurement, the fifth conductance measurement, and the sixth conductance measurement (an exemplary second calculation step 1224). In such a method 1200 embodiment, for example, third conductance measurement and the fourth conductance measurement may be indicative of one of a stenotic lesion or a non-stenotic region, and wherein the fifth conductance measurement and the sixth conductance measurement are indicative of the other of the stenotic lesion or the non-stenotic region. In another method 1200 embodiment, the third, fourth, fifth, and sixth conductance measurements may be all at a stenotic lesion or all at a non-stenotic region.

In various embodiments of methods 1200 of the present disclosure, calculation step 1214 and/or second calculation step 1224 is/are performed to calculate a size parameter selected from the group consisting of a cross-sectional area, a diameter, and a radius. For example, and as referenced above, the conductivity of the first/injected fluid ($\sigma_{fluid}$ or $\sigma_{saline}$) can be known or determined from calibration, the conductivity of fluid native to the mammalian luminal organ ($\sigma_{native}$ or $\sigma_{blood}$ if the native fluid is blood) can be determined from the first conductivity measurement and the second conductivity measurement, with the conductance measurements inside and outside of outer sheath 1175, as referenced above, are obtained by performing exemplary method steps. In view of the same, a mammalian luminal organ cross-sectional area (CSA) can be determined as follows:

$$CSA = [(L \times (G_{saline} - G_{blood}))/(\sigma_{saline} - \sigma_{blood})] \quad [17]$$

A luminal organ diameter (D) can then be determined as follows:

$$D = \sqrt{(4/\pi) \times CSA} \quad [18]$$

whereby the radius (R) can be determined by dividing D by two.

As referenced above, various method 1200 steps can be performed to obtain conductance measurements at various locations. Obtaining conductance measurements, and subsequently using the same to determine cross-sectional areas (CSAs) at, for example, a non-stenotic region and at a stenotic region within a mammalian luminal organ can provide useful data in connection with the degree of vessel blockage, sizing data so that an appropriately sized-stent could be used, etc., to facilitate improved patient treatment.

In at least another method 1200 of the present disclosure, method 1200 comprises an exemplary introduction step 1202, an exemplary first conductance measurement step 1204, an exemplary third conductance measurement step 1210, and an exemplary fourth conductance measurement step 1212. In such an embodiment, steps 1204, 1210, and 1212 can be performed in any order, such as in the order of steps 1204, 1210, and 1212, in the order of 1210, 1212, and 1204, or in another order, so long as the performance of steps 1204, 1210, 1212 are performed to obtain $g_{blood}$ and $G_{blood}$ (if the measurements are obtained in the presence of blood) and $G_{saline}$ (if the measurements are obtained in the presence of saline). In addition, and in at least one embodiment of such a method, $g_{saline}$ (if in the presence of saline) may be a constant or may be a known variable based upon, for example, one or more prior saline injections through device 1150.

Figure 12:
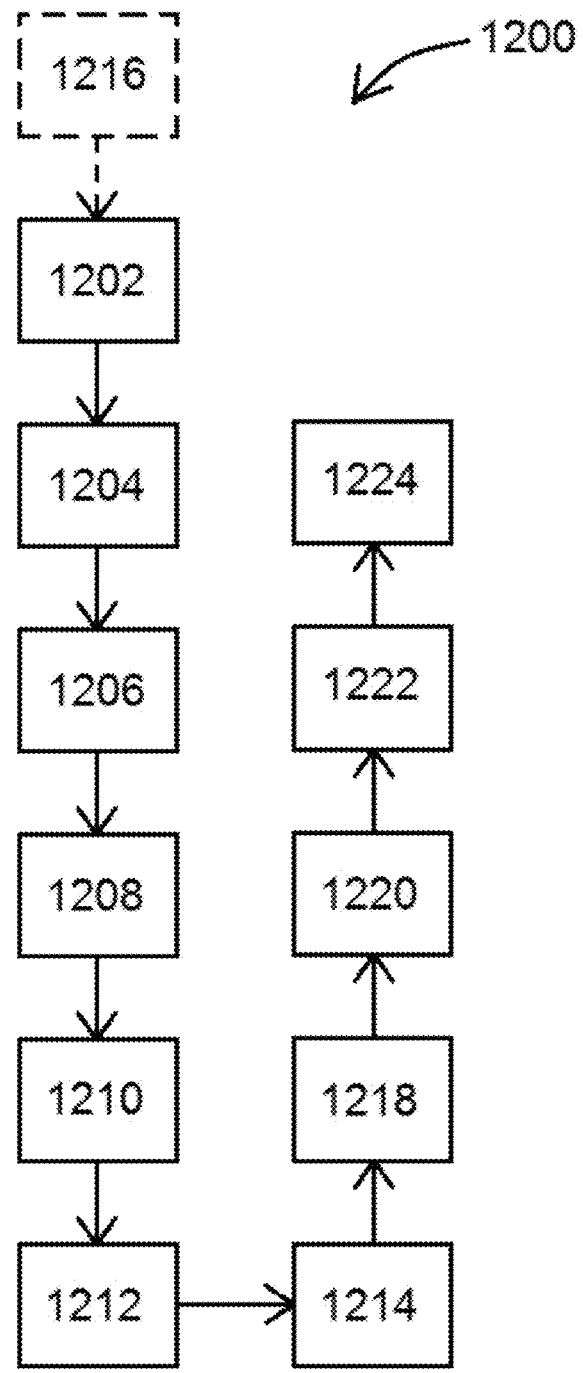
FIG. 12 shows a block diagram of steps of performing an exemplary method using an exemplary device of the present disclosure.

The various methods 1200 of the present disclosure referenced herein and as shown in FIG. 12 may be performed in one or more different orders than originally described or shown. For example, and as shown in FIG. 12, steps 1204, 1206, 1210, and 1212 are performed in that order, where measurements are obtained with a native fluid, saline, native fluid, and saline, in that order. However, said steps could also be performed in a different order within the scope of the present application. For example, step 1206 could be performed first, then 1204, and then 1210 and 1212 in either order. Furthermore, the terms "first," "second," "third," etc., are used herein to refer to conductance measurements, but are also terms commonly used to indicate a particular order. As such, and for example, an exemplary third conductance measurement step 1210 may be the third measurement obtained in a particular method 1200 embodiment, or it may be, for example, the first, second, third, etc., measurement obtained.

Figure 13:
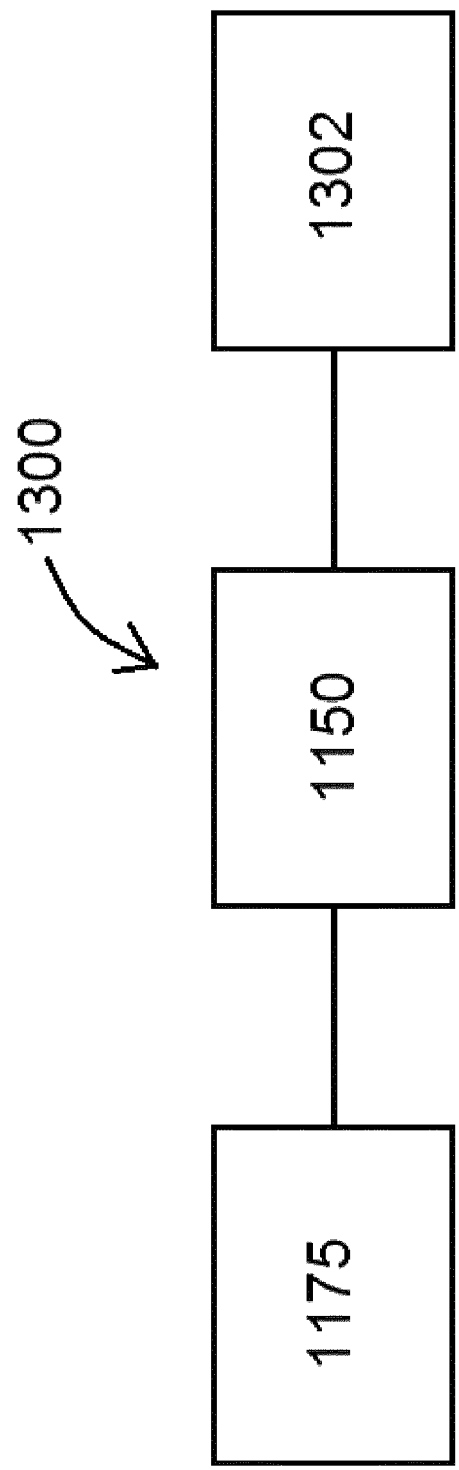
FIG. 13 shows a block diagram of components of an impedance system, according to an embodiment of the present disclosure.

As referenced above, and as shown in the block diagram of FIG. 13, an exemplary device 1150 can be used with a data acquisition and processing system 1302 (also referenced as a "Data Processing Unit" in FIG. 3), which is operable to obtain and process data from device 1150. In at least one embodiment, one or more additional components shown in FIG. 3, such as "PC" 157, "A-D Conversion Unit" 153, and others, can be used on connection with data acquisition and processing system 1302, and/or can be part of with data acquisition and processing system 1302. In at least one embodiment of an impedance system 1300 of the present disclosure (which may also be catheter 20 plus one or more other components as shown in FIG. 3), and as shown in FIG. 13, impedance system 1300 comprises impedance device 1150, outer sheath 1175, and optionally data acquisition and processing system 1302.

Again, it is noted that the various devices, systems, and methods described herein can be applied to any body lumen or treatment site. For example, the devices, systems, and methods described herein can be applied to any one of the following exemplary bodily hollow organs: the cardiovascular system including the heart, the digestive system, the respiratory system, the reproductive system, and the urogenital tract.

While various embodiments of impedance devices for obtaining conductance measurements within luminal organs have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for obtaining one or more conductance measurements using an impedance device, the method comprising the steps of:

introducing at least part of an impedance device into a mammalian luminal organ, the impedance device comprising an elongated body and a detector positioned along the elongated body;

obtaining a first conductance measurement using the detector while the detector is surrounded by an outer sheath surrounding at least part of the impedance device, the first conductance measurement indicative of a fluid native to the mammalian luminal organ present within a lumen of the outer sheath;

obtaining a second conductance measurement using the detector while the detector is surrounded by the outer sheath, the second conductance measurement indicative of a first injection of a first solution of a first compound through the lumen of the outer sheath;

moving the impedance device and/or the outer sheath relative to one another so that the outer sheath no longer surrounds the detector;

obtaining a third conductance measurement using the detector, the third conductance measurement indicative of the fluid native to the mammalian luminal organ;

obtaining a fourth conductance measurement using the detector, the fourth conductance measurement indicative of a second injection of the first solution through the lumen of the outer sheath; and calculating a size parameter of the mammalian luminal organ based in part upon the third conductance measurement, the fourth conductance measurement, and a conductivity of the fluid native to the mammalian luminal organ determined in part from the first conductance measurement.

2. The method of claim 1, wherein the step of introducing the at least part of the impedance device is performed using access through a patient's femoral artery and advancement to a location of interest within the mammalian luminal organ.

3. The method of claim 1, wherein the step of obtaining the first conductance measurement is performed while an aperture defined within the outer sheath is opened to allow the fluid native to the mammalian luminal organ to flow within the lumen of the outer sheath.

4. The method of claim 1, wherein the step of obtaining the first conductance measurement is performed while the fluid native to the mammalian luminal organ is pulled into the lumen of the outer sheath using suction.

5. The method of claim 1, wherein the step of obtaining the second conductance measurement is performed when a desired temperature local to the detector is achieved, the desired temperature indicative of the first injection of the first solution.

6. The method of claim 5, wherein the desired temperature is determined using a temperature sensor coupled to the impedance device at or near the detector.

7. The method of claim 1, wherein the step of obtaining the second conductance measurement is performed when a threshold conductance is achieved, the threshold conductance indicative of a conductance sufficiently different from the first conductance measurement.

8. The method of claim 1, further comprising the step of:
calibrating the impedance device prior to the step of introducing the at least part of the impedance device into the mammalian organ, the step of calibrating performed by operating the device within a plurality of phantoms of known sizes in the presence of the first solution to determine a conductivity of the first solution.

9. The method of claim 8, wherein the step of calculating a size parameter is performed using the conductivity of the fluid native to the mammalian luminal organ which is further determined from the second conductance measurement and the conductivity of the first solution.

10. The method of claim 9, wherein the step of calculating a size parameter is performed using the conductivity of the fluid native to the mammalian luminal organ which is further determined using a known inner cross-sectional area of the outer sheath and a known distance between detection electrodes of the detector.

11. The method of claim 1, wherein the step of calculating a size parameter is performed using the conductivity of the fluid native to the mammalian luminal organ which is further determined using a known inner cross-sectional area of the outer sheath and a known distance between detection electrodes of the detector.

12. The method of claim 11, wherein the step of obtaining the fourth conductance measurement is performed by obtaining a plurality of fourth conductance measurements over time.

13. The method of claim 1, wherein the step of obtaining the fourth conductance measurement is performed when a desired temperature local to the detector is achieved, the desired temperature indicative of the second injection of the first solution.

14. The method of claim 1, wherein the step of calculating a size parameter is further based in part upon a known distance between detection electrodes of the detector.

15. The method of claim 1, wherein the introducing step is performed by introducing an impedance device selected from the group consisting of an impedance catheter and an impedance wire into the mammalian luminal organ, wherein the impedance device is at least partially surrounded by an outer sheath selected from the group consisting of catheter and a non-catheter sheath.

16. The method of claim 1, wherein the step of introducing is performed by introducing the at least part of the impedance device into the mammalian luminal organ at a stenosis, whereby the impedance device can be used to perform one or more of the steps of obtaining a third conductance measurement and/or obtaining a fourth conductance measurement at the stenosis.

17. The method of claim 1, wherein the step of introducing is performed by introducing the at least part of the impedance device into the mammalian luminal organ at a stenosis, and wherein the method further comprises the steps of:
moving the at least part of the impedance device to a second location within the mammalian luminal organ;
obtaining a fifth conductance measurement using the detector, the fifth conductance measurement indicative of the fluid native to the mammalian luminal organ at the second location;
obtaining a sixth conductance measurement using the detector, the sixth conductance measurement indicative of a third injection of the first solution through the lumen of the outer sheath; and
calculating a second size parameter of the mammalian luminal organ at the second location based in part upon the fifth conductance measurement and the sixth conductance measurement;
wherein the third conductance measurement and the fourth conductance measurement are indicative of one of a stenotic lesion or a non-stenotic region, and wherein the fifth conductance measurement and the sixth conductance measurement are indicative of the other of the stenotic lesion or the non-stenotic region.

18. The method of claim 1, wherein the step of calculating a size parameter is performed to calculate a size parameter selected from the group consisting of a cross-sectional area, a diameter, and a radius.

19. A method for obtaining one or more conductance measurements using an impedance device, the method comprising the steps of:
introducing at least part of an impedance device into a mammalian luminal organ, the impedance device comprising an elongated body and a detector positioned along the elongated body;
obtaining a first conductance measurement using the detector while the detector is surrounded by an outer sheath surrounding at least part of the impedance device, the first conductance measurement indicative of blood from the mammalian luminal organ present within a lumen of the outer sheath;
moving the impedance device and/or the outer sheath relative to one another so that the outer sheath no longer surrounds the detector;
obtaining a second conductance measurement using the detector, the second conductance measurement indicative of the blood;

obtaining a third conductance measurement using the detector, the third conductance measurement indicative of an injection of saline through the lumen of the outer sheath; and calculating a size parameter of the mammalian luminal organ based in part upon the second conductance measurement, the third conductance measurement, and a known distance between detection electrodes of the detector.

20. The method of claim 19, wherein the introducing step is performed by introducing an impedance device selected from the group consisting of an impedance catheter and an impedance wire into the mammalian luminal organ, wherein the impedance device is at least partially surrounded by an outer sheath selected from the group consisting of catheter and a non-catheter sheath.

21. A method for obtaining one or more conductance measurements using an impedance device, the method comprising the steps of:

introducing at least part of an impedance device into a mammalian luminal organ, the impedance device comprising an elongated body and a detector positioned along the elongated body;

obtaining a first conductance measurement using the detector while the detector is surrounded by an outer sheath surrounding at least part of the impedance device, the first conductance measurement indicative of a fluid native to the mammalian luminal organ present within a lumen of the outer sheath;

obtaining a second conductance measurement using the detector while the detector is surrounded by the outer sheath, the second conductance measurement indicative of a first injection of a first solution of a first compound through the lumen of the outer sheath;

moving the impedance device and/or the outer sheath relative to one another so that the outer sheath no longer surrounds the detector;

obtaining a third conductance measurement using the detector, the third conductance measurement indicative of the fluid native to the mammalian luminal organ;

obtaining a fourth conductance measurement using the detector, the fourth conductance measurement indicative of a second injection of the first solution through the lumen of the outer sheath;

moving the at least part of the impedance device to a second location within the mammalian luminal organ;

obtaining a fifth conductance measurement using the detector, the fifth conductance measurement indicative of the fluid native to the mammalian luminal organ at the second location;

obtaining a sixth conductance measurement using the detector, the sixth conductance measurement indicative of a third injection of the first solution through the lumen of the outer sheath;

calculating a first size parameter of the mammalian luminal organ based in part upon the third conductance measurement, the fourth conductance measurement, and a conductivity of the fluid native to the mammalian luminal organ determined in part from the first conductance measurement; and calculating a second size parameter of the mammalian luminal organ at the second location based in part upon the fifth conductance measurement and the sixth conductance measurement.

* * * * *